(12) United States Patent
O'Halloran

(10) Patent No.: US 9,938,573 B2
(45) Date of Patent: *Apr. 10, 2018

(54) METHODS AND KITS FOR NUCLEIC ACID SEQUENCING

(71) Applicant: QuantuMDx Group Limited, Newcastle upon Tyne (GB)

(72) Inventor: Jonathan O'Halloran, Uckfield (GB)

(73) Assignee: QUANTUMDX GROUP LIMITED, Newcastle Upon Tyne (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/228,950

(22) Filed: Aug. 4, 2016

(65) Prior Publication Data

US 2017/0037463 A1    Feb. 9, 2017

Related U.S. Application Data

(63) Continuation of application No. 13/062,208, filed as application No. PCT/IB2009/006976 on Sep. 3, 2006, now Pat. No. 9,410,196.

(60) Provisional application No. 61/094,006, filed on Sep. 3, 2008, provisional application No. 61/094,025, filed on Sep. 3, 2008.

(51) Int. Cl.
*C12Q 1/68* (2006.01)
*G01N 33/487* (2006.01)

(52) U.S. Cl.
CPC ..... *C12Q 1/6869* (2013.01); *G01N 33/48721* (2013.01)

(58) Field of Classification Search
CPC .................................................. C12Q 1/6869
USPC .................... 435/6.12, 91.2, 287.2
See application file for complete search history.

(56) References Cited

U.S. PATENT DOCUMENTS

| | | |
|---|---|---|
| 6,310,189 B1 | 10/2001 | Fodor et al. |
| 8,871,921 B2 | 10/2014 | O'Halloran |
| 2001/0036672 A1 | 11/2001 | Anderson et al. |
| 2003/0104437 A1 | 6/2003 | Barnes et al. |
| 2003/0215816 A1 | 11/2003 | Sundararajan et al. |
| 2005/0123958 A1 | 6/2005 | Tsuchiya |
| 2005/0164205 A1 | 7/2005 | Puskas |
| 2007/0190546 A1 | 8/2007 | Siddiqi et al. |
| 2007/0238186 A1 | 10/2007 | Sun et al. |
| 2010/0035260 A1 | 2/2010 | Olasagasti et al. |
| 2010/0093992 A1 | 4/2010 | Cherkasov et al. |
| 2011/0165572 A1 | 7/2011 | O'Halloran |
| 2012/0074925 A1 | 3/2012 | Oliver |
| 2015/0259731 A1 | 9/2015 | O'Halloran |
| 2015/0276709 A1 | 10/2015 | O'Halloran et al. |

FOREIGN PATENT DOCUMENTS

| | | |
|---|---|---|
| CN | 1617937 | 5/2005 |
| CN | 10184853 | 5/2008 |
| CN | 202284206 U | 6/2012 |
| CN | 101076537 B | 7/2012 |
| CN | 102242062 A | 12/2012 |
| JP | 2005-503114 | 2/2005 |
| JP | 2005-511058 | 4/2005 |
| JP | 2005-526512 | 9/2005 |
| JP | 2007-195548 | 8/2007 |
| JP | 2008-534018 | 8/2008 |
| WO | 97/28282 A1 | 8/1997 |
| WO | 02/063030 A2 | 8/2002 |
| WO | 03/052139 A1 | 6/2003 |
| WO | 03048387 | 6/2003 |
| WO | 03/091406 A2 | 11/2003 |
| WO | 03/100096 A1 | 12/2003 |
| WO | 2006001944 A1 | 1/2006 |
| WO | 2006/095981 A1 | 9/2006 |
| WO | 2006/097320 A2 | 9/2006 |
| WO | 2006/105360 A1 | 10/2006 |
| WO | 2007062160 | 5/2007 |
| WO | 2007/077952 A1 | 7/2007 |
| WO | WO 2008/070749 | 6/2008 |
| WO | 2008079169 A2 | 7/2008 |
| WO | 2009/006445 A2 | 1/2009 |
| WO | 2010002939 A2 | 1/2010 |
| WO | 2010/026488 A2 | 3/2010 |
| WO | 2010/028140 A2 | 3/2010 |
| WO | WO 2010/026490 | 3/2010 |
| WO | WO 2014/024041 | 2/2014 |

OTHER PUBLICATIONS

International Search Report and Written Opinion dated Apr. 28, 2017 in International Application No. PCT/US2017/012065, filed Jan. 3, 2017 in 14 pages.
Notice of Allowance dated May 8, 2017 in Japanese Application No. 2015-132532.
Reexamination Notification dated May 26, 2017 in Chinese Application No. 200980142508.2, filed Sep. 3, 2009.
Office Action dated Jul. 15, 2016 in Japanese Patent Application No. 2015-133481, in 15 pages.
Rejection Decision in Chinese Patent Application 200980142508.2, dated Jul. 4, 2016 in 17 pages.
Kumar et al. "Terminal Phosphate Labeled Nucleotides: Synthesis, Applications, and Linker Effect on Incorporation by DNA Polymerases", Nucleosides, Nucleotides and Nucleic Acids, 24 pp. 401-408, 2005.
Stratagene Catalog, 1988, p. 39.
Costa et al., Characterization in vitro and in vivo of the putative multigene 4-coumarate: CoA ligase network in *Arabidopsis*: syringyl lignin and sinapate/sinapyl alcohol derivative formation, Phytochemistry, Sep. 1, 2005, vol. 66, No. 17, pp. 2072-2091.
Zhu, Z. et al., "Molecular mechanism controlling the incorporation of fluorescent nucleotides into DNA by PCR," Cytometry, Jan. 1, 1997, vol. 28, pp. 206-211.
Barrato, C., et al. "SnO2 nanowire bio-transistor for electrical DNA sensing", IEEE Sensors 2007 Conference, pp. 1132-1135.

(Continued)

*Primary Examiner* — Jezia Riley
(74) *Attorney, Agent, or Firm* — Knobbe, Martens, Olson & Bear, LLP

(57) ABSTRACT

Various embodiments of the present disclosure generally relate to molecular biological protocols, equipment and reagents for the sequencing of target nucleic acid (DNA, RNA, cDNA, etc) molecules.

19 Claims, 7 Drawing Sheets

(56) References Cited

OTHER PUBLICATIONS

Cui, Y., et al. "Nanowire Nanosensors for Highly Sensitive and Selective Detection of Biological and Chemical Species", Science, vol. 293, Aug. 17, 2001, pp. 1289-1292.

Maki, W.C. et al., Universal bio-molecular signal transduction-based nano-electronic bio-detection system, Sensors and Actuators B, Aug. 12, 2008, vol. 133, No. 2, pp. 547-554.

Star, A. et al., Label-free detection of DNA hybridization using carbon nanotube network field-effect transistors, Proceedings of the National Academy of Sciences of USA, Jan. 24, 2006, vol. 103, No. 4, pp. 921-926.

Wu, F. Y.-H., et al., "Synthesis and properties of adenosine-5'-triphosphoro-gamma-1-(5-sulfonic acid)naphthyl ethylamidate: A fluorescent nucleotide substrate for DNA-dependent RNA polymerase from *Escherichia coli*," Archives of Biochemistry and Biophysics, May 1, 1986, vol. 246, No. 2, pp. 564-571.

International Search Report dated Mar. 3, 2010, for International Application No. PCT/IB2009/006976.

International Search Report dated Feb. 19, 2010, for International Application No. PCT/IB2009/005008.

International Search Report dated Feb. 17, 2010, for International Application No. PCT/IB2009/007025.

Office Action dated Jun. 23, 2017 in corresponding Indian Application No. 1752/DELNP/2011, filed Sep. 3, 2009.

METHODS AND KITS FOR NUCLEIC ACID SEQUENCING

CROSS REFERENCE TO RELATED APPLICATIONS

This application is a Continuation application of U.S. application Ser. No. 13/062,208, filed Mar. 3, 2011 which is the national phase under 35 U.S.C. § 371 of prior PCT International Application No. PCT/IB2009/006976 which has an International filing date of Sep. 3, 2009, designating the United States of America, which claims the benefit of U.S. Provisional Patent Application Nos. 61/094,006 and 61/094,025 filed on Sep. 3, 2008, the disclosures of which are hereby expressly incorporated by reference in their entirety and are hereby expressly made a portion of this application.

REFERENCE TO SEQUENCE LISTING

The present application is being filed along with a Sequence Listing in electronic format. The Sequence Listing is provided as file SequenceListing_QMDX.001C1.TXT created and last modified on Oct. 17, 2016, which is 622 bytes in size. The information in the electronic format of the Sequence Listing is incorporated herein by reference in its entirety.

BACKGROUND OF THE INVENTION

Field of the Invention

The present invention relates to molecular biological methods, equipment and reagents for sequencing target nucleic acid (DNA, RNA, cDNA, etc) molecules to enable both highly parallel and long 'read-length' nucleotide sequencing.

Description of the Related Art

DNA is a long polymer consisting of units called nucleotides. The DNA polymers are long chains of single units, which together form molecules called nucleic acids. Nucleotides can be one of four subunits (adenine (A), cytosine (C), guanine (G) & thymine (T)) and, when in a polymer, they may carry the genetic information in the cell. DNA comprises two long chains of nucleotides comprising the four different nucleotides bases (e.g. AGTCATCGTAGCT (SEQ ID NO: 1) . . . etc) with a backbone of sugars and phosphate groups joined by ester bonds, twisted into a double helix and joined by hydrogen bonds between the complementary nucleotides (A hydrogen bonds to T and C to G in the opposite strand). The sequence of nucleotide bases along the backbone may determine individual hereditary characteristics.

The central dogma of molecular biology generally describes the normal flow of biological information: DNA can be replicated to DNA, the genetic information in DNA can be 'transcribed' into mRNA, and proteins can be translated from the information in mRNA, in a process called translation, in which protein subunits (amino acids) are brought close enough to bond, in order (as dictated by the sequence of the mRNA & therefore the DNA) by the binding of tRNA (each tRNA carries a specific amino acid dependant on its sequence) to the mRNA.

SUMMARY OF THE INVENTION

A method of sequencing a target polynucleotide is disclosed in accordance with embodiments of the present invention. The method comprises: providing within an assay region a sensitive detection nanostructure that generates a signal related to a property of the nanostructure within the assay region, wherein the nanostructure is coupled to a means for detecting the signal; hybridizing within the assay region a primer to the 5' end region of the target polynucleotide, such that the resulting primer-target polynucleotide is operably coupled to the nanostructure; adding one or more nucleotides and a polymerase to the primer-target polynucleotide within the assay region under conditions that support polymerization of a nascent chain when at least one of the added nucleotides is complimentary to the base on the target polynucleotide downstream of the primer; and detecting within the assay region a change in the signal that is characteristic of the at least one nucleotide added to the nascent chain.

In preferred embodiments of the method, the property of the nanostructure is an electrical charge.

In certain embodiments of the method, the added nucleotide further comprises a charge mass reporter moiety comprising a high charge mass moiety and a linker. In some embodiments, the charge mass reporter moiety is configured to be removable. In some embodiments, the charge mass reporter moiety is removed from the added nucleotide after detecting the signal. In some other embodiments, the charge mass reporter moiety is configured not to affect polymerization of the nascent chain by the polymerase. In yet other embodiments, the charge mass reporter moiety is configured to protrude out from the nascent chain so as to reach-down to the sensitive detection nanostructure.

In some embodiments, the high charge mass moiety comprises an aromatic and/or aliphatic skeleton comprising one or more of a tertiary amino group, an alcohol hydroxyl group, a phenolic hydroxy group, or any combinations thereof. The high charge mass moiety may comprise one or more of the following groups or derivatives thereof:

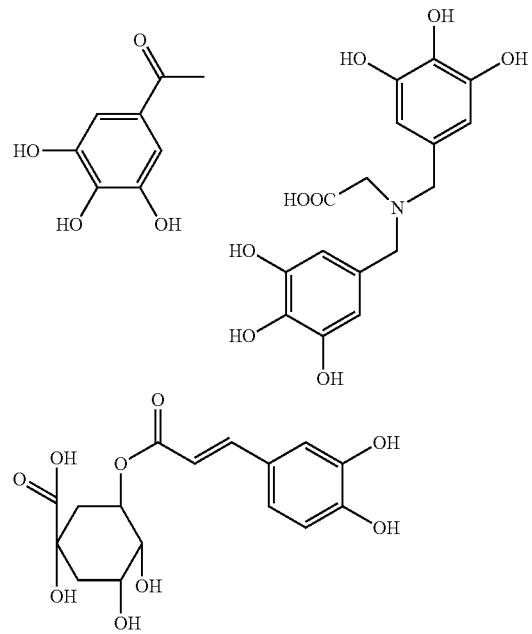

In certain embodiments of the method, the linker comprises a molecule of the following general formula:

wherein L comprises a linear or branched chain comprising an alkyl group, an oxy alkyl group, or a combination thereof.

In some embodiments, L may comprise a linear chain comprising an alkyl group, an oxy alkyl group, or a combination thereof. The number of carbon atoms in the linear chain may be 1 to 100.

In some embodiments, the added nucleotide may also comprise a cleavable cap molecule at the 5' phosphate so that addition of another nucleotide is prevented until the cleavable cap is removed. In some other embodiments, the linker can be bound to the 5' phosphate group of the added nucleotide, thereby acting as a cap.

In variations to the method, more than one nucleotide may be added to the assay region, but a successive nucleotide is not added to the nascent chain until after the signal that is characteristic of the preceding nucleotide added to the nascent chain is detected.

In some embodiments, the operable coupling between the primer-target polynucleotide and the nanostructure comprises immobilization of the primer to the sensitive detection nanostructure. In other embodiments, the operable coupling between the primer-target polynucleotide and the nanostructure comprises immobilization of the target polynucleotide to the sensitive detection nanostructure.

In certain embodiments, hybridizing the primer to the 5' end region of the target polynucleotide comprises hybridizing the primer to an oligonucleotide that has been ligated to the 5' end of the target polynucleotide.

In certain embodiments, the sensitive detection nanostructure is selected from the group consisting of a nanowire, a nanotube, a nanogap, a nanobead, a nanopore, a field effect transistor (FET)-type biosensor, a planar field effect transistor, and any conducting nanostructures.

The target polynucleotide and the primer preferably comprise molecules selected from the group consisting of DNA, RNA, peptide nucleic acid (PNA), morpholino, locked nucleic acid (LNA), glycol nucleic acid (GNA), threose nucleic acid (TNA), synthetic nucleotide polymer, and derivatives thereof. The added nucleotide preferably comprises a molecule selected from the group consisting of a deoxyribonucleotide, a ribonucleotide, a peptide nucleotide, a morpholino, a locked nucleotide, a glycol nucleotide, a threose nucleotide, a synthetic nucleotide, and derivatives thereof.

In some embodiments, the means for detecting the signal are selected from the group consisting of piezoelectric detection, electrochemical detection, electromagnetic detection, photodetection, mechanical detection, acoustic detection and gravimetric detection.

An apparatus for sequencing a target polynucleotide is disclosed in accordance with other embodiments of the present invention. The apparatus comprises: an assay region comprising a sensitive detection nanostructure capable of generating a signal related to the electrical charge of the nanostructure, and a signal detection means coupled to the sensitive detection nanostructure. In some embodiments, the apparatus may further comprise a pico-well or a microfluidics channel, arrayed with the sensitive detection nanostructures, wherein the biological sample comprises any body fluid, cells and their extract, tissues and their extract, and any other biological sample comprising nucleotides. In some other embodiments, the apparatus may comprise a microfluidics cassette. The microfluidics cassette may comprise a sample reception element for introducing a biological sample comprising the target polynucleotide into the cassette; a lysis chamber for disrupting the biological sample to release a soluble fraction comprising nucleic acids and other molecules; a nucleic acid separation chamber for separating the nucleic acids from the other molecules in the soluble fraction; an amplification chamber for amplifying the target polynucleotide; an assay region comprising an array of one or more sensitive detection nanostructures that generate a signal related to a property of the nanostructures, wherein the assay region is configured to allow operable coupling of the target polynucleotide to the nanostructures; and a conducting element for conducting the signal to a detector. In some examples, the apparatus can be used for the biological sample, which can be any body fluid, cells and their extract, tissues and their extract, and any other biological sample comprising the target polynucleotide. The apparatus for sequencing disclosed in some embodiments herein can be is sized and configured to be handheld.

DETAILED DESCRIPTION OF THE PREFERRED EMBODIMENT

Figure 1:
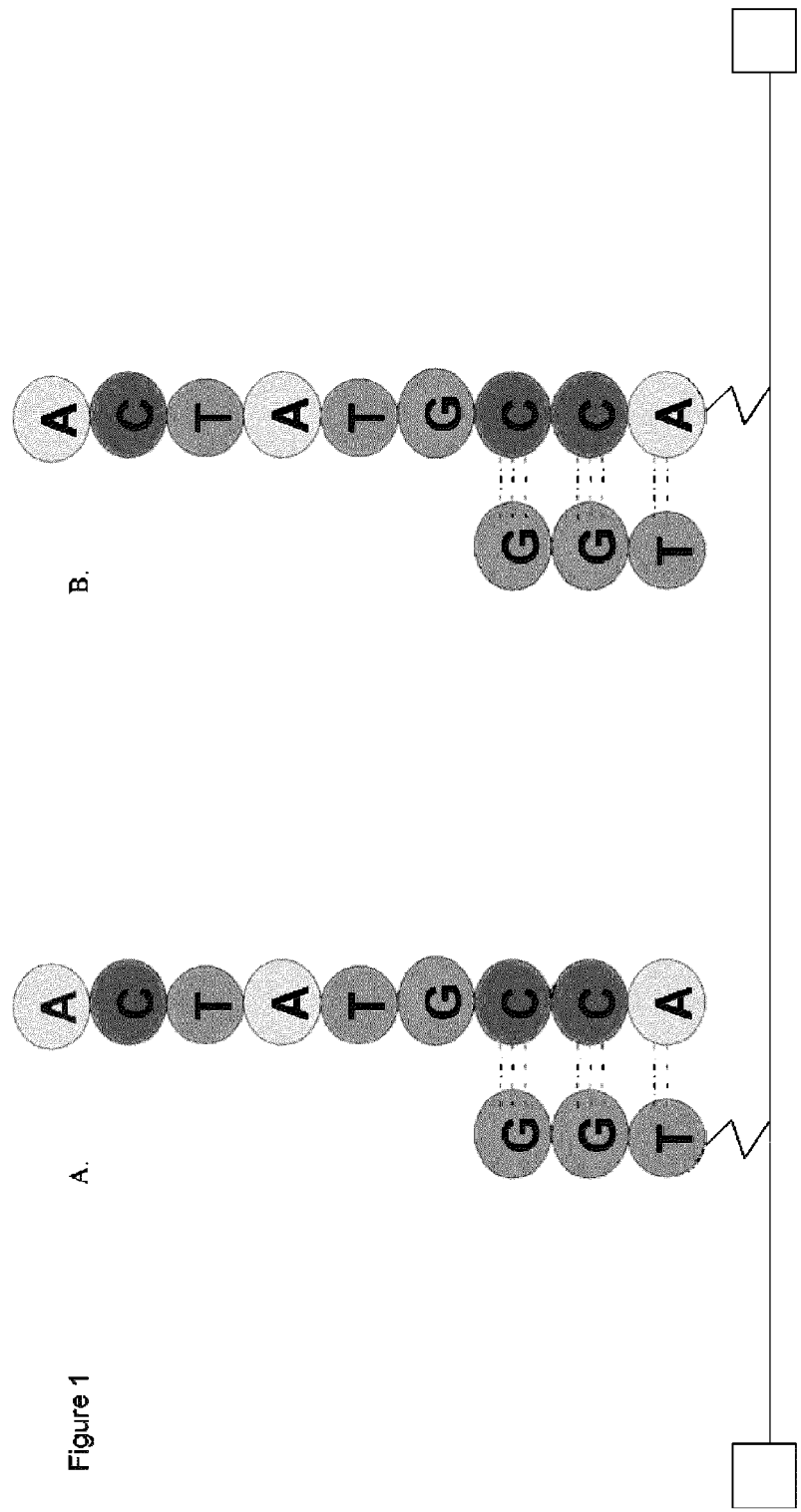
FIGS. 1 A and B are depictions of an illustrative embodiment of immobilization of a probe sequence and a measurement of a target DNA.

The term nucleotide sequencing generally encompasses biochemical methods for determining the order of the nucleotide bases, adenine, guanine, cytosine, and thymine, in DNA or RNA molecules. The sequence of DNA constitutes the heritable genetic information in genomes, plasmids, mitochondria, and chloroplasts that forms the basis for the developmental programs of living organisms. Genetic variations can cause disease, or confer an increased risk of disease (although it is also true that certain genetic variations confer beneficial traits). These variations can be inherited (passed on by parents) or acquired (developed as an adult). It is therefore of significant importance to know the sequence of these genetic molecules to gain a better understanding of life, molecular systems and disease.

The advent of DNA sequencing has significantly accelerated biological research and discovery. The rapid speed of sequencing attainable with modern DNA sequencing technology has been instrumental in the large-scale sequencing of the human genome, in the Human Genome Project. Related projects have generated the complete DNA sequences of many animal, plant, viral, and microbial genomes.

RNA sequencing, which for technical reasons is easier to perform than DNA sequencing, was one of the earliest forms of nucleotide sequencing. The major landmark of RNA sequencing, dating from the pre-recombinant DNA era, is the sequence of the first complete gene and then the complete genome of Bacteriophage MS2, identified and published by Walter Fiers and his coworkers at the University of Ghent (Ghent, Belgium), published between 1972 and 1976.

The chain-termination method developed by Frederick Sanger and co-workers in 1975 was the first method of DNA sequencing to be employed on a large scale. Prior to the development of rapid DNA sequencing methods in the early 1970s by Sanger in England and Walter Gilbert and Allan Maxam at Harvard, a number of laborious methods were used. For instance, in 1973 Gilbert and Maxam reported the sequence of 24 base-pairs using a method known as wandering-spot analysis.

In 1976-1977, Allan Maxam and Walter Gilbert developed a DNA sequencing method based on chemical modification of DNA and subsequent cleavage at specific bases. The method requires radioactive labelling at one end of the DNA strand and purification of the DNA fragment to be sequenced. In frequent breaks are generated at one and sometimes two of the four nucleotide bases and this repeated in four reactions (G, A+G, C, C+T). This produces a series of labelled fragments, from the radiolabelled end to the first 'cut' site in each molecule and size-separated by gel electrophoresis, with the four reactions arranged side by side. Maxam-Gilbert sequencing was not readily taken up due to its technical complexity, extensive use of hazardous chemicals, and difficulties with scale-up. In addition, the method cannot easily be customized for use in a standard molecular biology kit.

The chain-termination or Sanger method requires a single-stranded DNA template, a DNA primer, a DNA polymerase, radioactively or fluorescently labeled nucleotides, and modified nucleotides, dideoxynucleotides triphosphates (ddNTPs) that terminate DNA strand elongation. The DNA sample is divided into four separate sequencing reactions, containing the four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. Incorporation of a dideoxynucleotide into the nascent (elongating) DNA strand therefore terminates DNA strand extension, resulting in various DNA fragments of varying length. The dideoxynucleotides are added at lower concentration than the standard deoxynucleotides to allow strand elongation sufficient for sequence analysis.

The newly synthesized and labeled DNA fragments are heat denatured, and separated by size (with a resolution of just one nucleotide) by gel electrophoresis on a denaturing polyacrylamide-urea gel. Each of the four DNA synthesis reactions is run in one of four individual lanes (lanes A, T, G, C); the DNA bands are then visualized by autoradiography or UV light, and the DNA sequence can be directly read off the X-ray film or gel image. In the image on the right, X-ray film was exposed to the gel, and the dark bands correspond to DNA fragments of different lengths. A dark band in a lane indicates a DNA fragment that is the result of chain termination after incorporation of a dideoxynucleotide (ddATP, ddGTP, ddCTP, or ddTTP). The terminal nucleotide base can be identified according to which dideoxynucleotide was added in the reaction giving that band. The relative positions of the different bands among the four lanes are then used to read (from bottom to top) the DNA sequence as indicated.

DNA fragments can be labeled by using a radioactive or fluorescent tag on the primer, in the new DNA strand with a labeled dNTP, or with a labeled ddNTP. There are some technical variations of chain-termination sequencing. In one method, the DNA fragments are tagged with nucleotides containing radioactive phosphorus for radiolabeling. Alternatively, a primer labeled at the 5' end with a fluorescent dye is used for the tagging. Four separate reactions are still required, but DNA fragments with dye labels can be read using an optical system, facilitating faster and more economical analysis and automation. This approach is known as 'dye-primer sequencing'. The later development by L Hood and co-workers of fluorescently labeled ddNTPs and primers set the stage for automated, high-throughput DNA sequencing.

The different chain-termination methods have greatly simplified the amount of work and planning needed for DNA sequencing. For example, the chain-termination-based "Sequenase" kit from USB Biochemicals contains most of the reagents needed for sequencing, prealiquoted and ready to use. Some sequencing problems can occur with the Sanger method, such as non-specific binding of the primer to the DNA, affecting accurate read-out of the DNA sequence. In addition, secondary structures within the DNA template, or contaminating RNA randomly priming at the DNA template can also affect the fidelity of the obtained sequence. Other contaminants affecting the reaction may consist of extraneous DNA or inhibitors of the DNA polymerase.

An alternative to primer labelling is labelling of the chain terminators, a method commonly called 'dye-terminator sequencing'. One of major advantages of this method is that the sequencing can be performed in a single reaction, rather than four reactions as in the labeled-primer method. In dye-terminator sequencing, each of the four dideoxynucleotide chain terminators is labeled with a different fluorescent dye, each fluorescing at a different wavelength. This method is attractive because of its greater expediency and speed and is now the mainstay in automated sequencing with computer-controlled sequence analyzers (see below). Its potential limitations include dye effects due to differences in the incorporation of the dye-labelled chain terminators into the DNA fragment, resulting in unequal peak heights and shapes in the electronic DNA sequence trace chromatogram after capillary electrophoresis. The dye-terminator sequencing method, along with automated high-throughput DNA sequence analyzers, is now being used for the vast majority of sequencing projects, as it is both easier to perform and lower in cost than most previous sequencing methods.

Modern dye-terminator or chain-termination sequencing can produce a sequence that may have poor quality in the first 15-40 bases, a high quality region of 700-900 bases, and then quickly deteriorating quality. Automated DNA sequencing instruments (DNA sequencers) operating these methods can sequence up to 384 fluorescently labelled samples in a single batch (run) and perform as many as 24 runs a day. However, automated DNA sequencers may carry out only DNA-size-based separation (by capillary electrophoresis), detection and recording of dye fluorescence, and data output as fluorescent peak trace chromatograms. Sequencing reactions by thermocycling, clean-up and re-suspension in a buffer solution before loading onto the sequencer may be performed separately.

Recent so called NextGen sequencing technologies, are based on pyrosequencing these new high-throughput methods use methods that parallelize the sequencing process, producing thousands or millions of sequences at once.

As molecular detection methods are often not sensitive enough for single molecule sequencing, Helicos method may be an exception, most approaches use an in vitro cloning step to generate many copies of each individual molecule. Emulsion PCR is one method, isolating individual DNA molecules along with primer-coated beads in aqueous bubbles within an oil phase. A polymerase chain reaction (PCR) then coats each bead with clonal copies of the isolated library molecule and these beads are subsequently immobilized for later sequencing. Emulsion PCR is used in the methods published by Marguilis et al. (commercialized by 454 Life Sciences, acquired by Roche), Shendure and Porreca et al. (also known as "polony sequencing") and SOLiD sequencing, (developed by Agencourt and acquired by Applied Biosystems). Another method for in vitro clonal amplification is "bridge PCR", where fragments are amplified upon primers attached to a solid surface, developed and used by Solexa (now owned by Illumina). These methods both produce many physically isolated locations which each contain many copies of a single fragment. The single-molecule method developed by Stephen Quake's laboratory (later commercialized by Helicos) skips this amplification step, directly fixing DNA molecules to a surface.

Once clonal DNA sequences are physically localized to separate positions on a surface, various sequencing approaches may be used to determine the DNA sequences of all locations, in parallel. "Sequencing by synthesis", like the popular dye-termination electrophoretic sequencing, uses the process of DNA synthesis by DNA polymerase to identify the bases present in the complementary DNA molecule. Reversible terminator methods (used by Illumina and Helicos) use reversible versions of dye-terminators, adding one nucleotide at a time, detecting fluorescence corresponding to that position, then removing the blocking group to allow the polymerization of another nucleotide. Pyrosequencing (used by 454) also uses DNA polymerization to add nucleotides, adding one type of nucleotide at a time, then detecting and quantifying the number of nucleotides added to a given location through the light emitted by the release of attached pyrophosphates. "Sequencing by ligation" is another enzymatic method of sequencing, using a DNA ligase enzyme rather than polymerase to identify the target sequence. Used in the polony method and in the SOLiD technology offered by Applied Biosystems, this method uses a pool of all possible oligonucleotides of a fixed length, labeled according to the sequenced position. Oligonucleotides are annealed and ligated; the preferential ligation by DNA ligase for matching sequences results in a signal corresponding to the complementary sequence at that position.

Other methods of DNA sequencing may have advantages in terms of efficiency or accuracy. Like traditional dye-terminator sequencing, they are limited to sequencing single isolated DNA fragments. "Sequencing by hybridization" is a non-enzymatic method that uses a DNA microarray. In this method, a single pool of unknown DNA can be fluorescently labeled and hybridized to an array of known sequences. If the unknown DNA can hybridize strongly to a given spot on the array, causing it to "light up", then that sequence is inferred to exist within the unknown DNA being sequenced. Mass spectrometry can also be used to sequence DNA molecules; conventional chain-termination reactions produce DNA molecules of different lengths and the length of these fragments can then be determined by the mass differences between them (rather than using gel separation).

There are new proposals for DNA sequencing, which are in development, but remain to be proven. These include labeling the DNA polymerase (Visigen), reading the sequence as a DNA strand transits through nanopores, or using nano-edge probe arrays that are stepped with sub-Angstrom resolution over a stretched and immobilized ssDNA (Reveo), a technique that uses single-photon detection, fluorescent labelling and DNA electrophoresis with detection using plasmonic nanostructures (base4innovation), and microscopy-based techniques, such as AFM or electron microscopy that are used to identify the positions of individual nucleotides within long DNA fragments by nucleotide labeling with heavier elements (e.g., halogens) for visual detection and recording.

With exception of methods using mass spec, nanopores and microscopy-based techniques, several methods presently available, or in development generally require the use of expensive optical equipment and complex software. Furthermore, mass spec, nanopores and microscopy-based techniques may require bulky equipment that may limit their deployment and certainly can drive costs up. Various embodiments used in connection with the present disclosure look to perform long read length, highly parallel, potentially single molecules sequencing in a portable and cost effect device using a novel sequencing by synthesis technique.

The sequencing of the human genome and the subsequent studies have since demonstrated the great value in knowing the sequence of a person's DNA. The information obtained by genomic DNA sequence analysis can provide information about an individual's relative risk of developing certain diseases (such as breast cancer and the BRCA 1&2 genes). Furthermore, the analysis of DNA from tumors can provide information about stage and grading.

Infectious diseases, such as those caused by viruses or bacteria also carry their genetic information in nucleotide polymer genomes (either DNA or RNA). Many of these have now been sequenced, (or enough of their genome sequenced to allow for a diagnostic test to be produced) and the analysis of infectious disease genomes from clinical samples (a field called molecular diagnostics) has become one of important methods of sensitively and specifically diagnosing disease.

Measurements of the presence or absence, as well as the abundance of mRNA species in samples can provide information about the health status of individuals, the disease stage, prognosis and pharmacogenetic and pharmacogenomic information. These expression arrays are fast becoming tools in the fight against complex disease and may gain in popularity as prices begin to fall.

In short, the analysis of nucleotide polymers (DNA & RNA) has become important in the clinical routine, however, cost remains a barrier to widespread global adoption. One reason for this is the complexity of the analysis requiring expensive devices that are able to sensitively measure up to four different fluorescence channels as RT-PCR experiments progress. The cheaper alternatives may require skilled technicians to run and interpret low-tech equipment, such as electrophoresis gels, but this too may be expensive and a lack of skilled technicians in developing countries is prohibitive.

To solve this, a method of nucleotide polymer analysis that may require cheap and easy to use devices may be required. Some embodiments of the present disclosure describes chemical reagents, synthetic nucleotides, that can generally be utilized in such devices. Various embodiments used in connection with of the present disclosure describes novel synthetic nucleotides that comprises at least some standard nucleotides (or any modifications, or isoforms), with a high negative charge mass reporter moiety attached via a linker molecule (for instance, attached to the 5' phosphate group), with the linker length of such a length so as to protrude from a polymerase complex during polymerization, so as not to cause a significant deleterious effect on the polymerase's action.

The terms nucleic acid or oligonucleotide or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp. 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

As used in various embodiments herein, a nucleotide can be, but not limited to, one of the following compounds, Adenine, Guanine, Cytosine, Thymine, Uracil, and Inosine as well as any modified nucleotides, any nucleotide derivatives and any degenerate base nucleotides.

Some non-limiting examples of such nucleotide may comprise a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof. Furthermore, single stranded deoxyribose nucleic acid (ssDNA) can generally be a single stranded nucleotide polymer molecule, comprising Nucleotides and double stranded deoxyribose nucleic acid (dsDNA) can generally be a double strand comprising two ssDNA molecules linked together via, for example, hydrogen bonding, in a reverse complimentary orientation.

Nucleotides can generally be synthesized through a variety of methods both in vitro and in vivo. This can involve salvage synthesis (the re-use of parts of nucleotides in resynthesizing new nucleotides through breakdown and synthesis reactions in order to exchange useful parts), or the use of protecting groups in a laboratory. In the latter case, a purified nucleoside or nucleobase can be protected to create a phosphoramidite, and can be used to obtain analogues not present in nature and/or to create an oligonucleotide.

In some embodiments, nucleotide synthesis comprises the formation of a nucleoside (the nitrogenous base joined to a sugar). The sugar involved in the synthesis and structure of a nucleotide may be either ribose or deoxyribose; in the latter case, the prefix 'deoxy' may be added before the name of the nucleoside in all cases except Uracil. A functional group of phosphate can be then esterified to the sugar, creating a nucleotide. The phosphate group may comprise one, two, or three phosphates, forming mono-phosphates, di-phosphates, or tri-phosphates, respectively.

Some other embodiments of the present disclosure describe the design, synthesis and use of special synthetic nucleotides comprising a nucleotide and a reporter moiety, in which the reporter moiety may not act as a polymerase enzyme blocking moiety attached via a linker.

In various embodiments, the synthetic nucleotides can have at least some of the following aspects:
1. The reporter moieties report based upon charge mass, not enzymatic activity, fluorescence etc so there can generally be more flexibility;
2. Each synthetic nucleotide may carry a different charge mass—although for simplicity initially the same charge mass can be used for proof of principle;
3. The reporter moieties may be easily cleaved; and/or
4. The nucleotides may be cheaply and easily mass synthesized.

The one of possible positions available for the attachment of linkers and the reporter moieties, so as to not interfere with polymerization or hydrogen bonding between the bases of nucleotides when hybridizing with its compliment base in another nucleotide polymer (i.e. when two strands of reverse compliment DNA hybridize to form a double stranded DNA molecule), can be the phosphate linkage in the nucleotide.

Some other embodiments describe methods of the use in which the linker and reporter moiety can be cleaved from the synthetic nucleotide in the iterative manner after detection; one of possible places to attach the linker can be the 5'-phosphate end of phosphate linkage.

Nature of linkage with the 5'-phosphate: There are at least two options available which could facilitate synthesis at the 5'-phosphate terminal:
1. Thiophosphate; and/or
2. Phosphoramidate.

The proposed linker therefore can have the following structure at least in some embodiments.

Where, L could be, but is not limited to, any linear or branched chain molecule that is configured to link to a nucleotide as well as a high charge mass moiety, both of which are present in a synthetic nucleotide. In some embodiments, L comprises a plurality of an alkyl group, an oxy alkyl group or the combination thereof with various lengths. In one embodiment, the number of an alkyl group, an oxy alkyl group or the combination thereof in L is 1 to 100. In another embodiment, the number of an alkyl group, an oxy alkyl group or the combination thereof in L is 1 to 75. In still another embodiment, the number of an alkyl group, an oxy alkyl group or the combination thereof in L is 1 to 50. In still embodiment, the number of an alkyl group, an oxy alkyl group or the combination thereof in L is 1 to 25. In some other embodiments, the number of an alkyl group, an oxy alkyl group and the combination thereof in L can be more than 100. While $NH_2$ is presented for the purpose of illustration, this $NH_2$ can be substituted with any other function group that can be cross-linked to a nucleotide or its derivative as well as a high charge mass moiety, both of which are present in a synthetic nucleotide. Some illustrative examples that can be used instead of $NH_2$ include, but not limited to, any alkyl group (e.g. $CH_{2+1}$, wherein n represents a positive integer number such as 1, 2, 3, and etc), any alcohol group (e.g. C—$H_2$—OH, wherein n represents a positive integer number such as 1, 2, 3, and etc), any carboxyl group (e.g. COOH), any amide group (e.g. CONH), and any derivatives thereof. As the linker molecules can vary in length and chemical structure in part to enable the reporter moiety to extend out from a nucleotide polymerase (e.g. DNA polymerase, RNA polymerase and others) complex so that some aspects of polymerization may not be influenced entirely or partially.

The easy access to the linkers of various lengths can be considered as a benefit in a situation where the desired length of the linker may not be known completely or partially. This may make the optimization experiments easy.

The linker with the nucleotide (say Adenosine as an illustrative example) therefore may have the following structure at least in some embodiments. While adenosine is presented in some examples below, this adenosine can be substituted with any other natural or synthetic nucleotide, any modifications thereof and any derivatives thereof in some other embodiments.

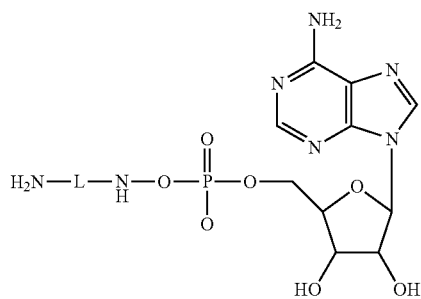

In some embodiments, various lengths of linkers at this position may have the following structures (exemplified with the Adenosine):

1. Ethylenediamine (2 carbon bond length separation)

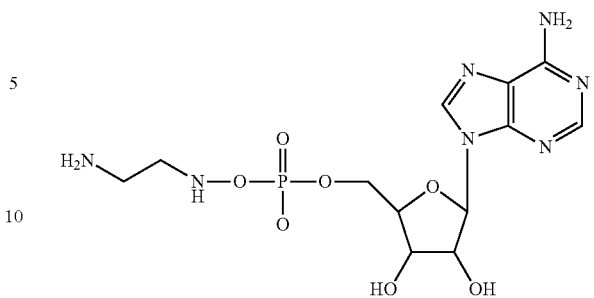

2. Pentanediamine (5 carbon bond length separation)

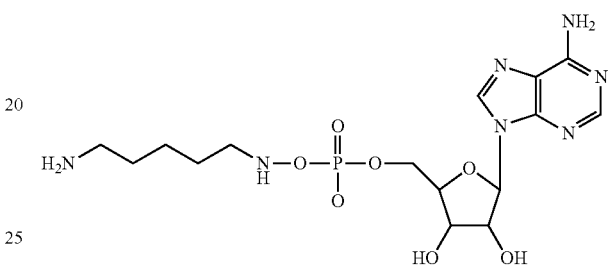

3. Length equivalent to 13 carbon bond length separation

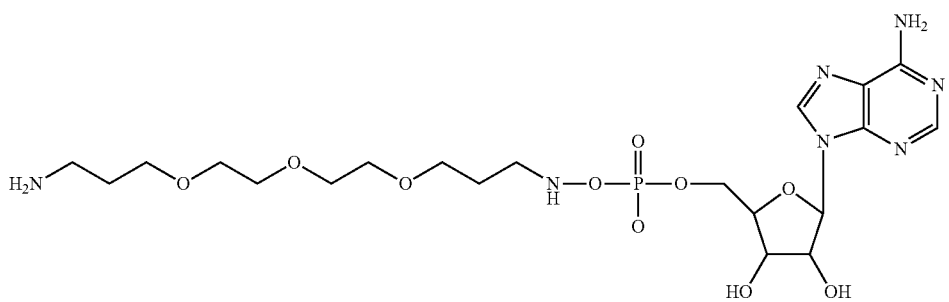 [SMILES: NCCCOCCOCCOCCCNOP(=O)(O)OCC1OC(n2cnc3c(N)ncnc32)C(O)C1O]

Thus in some embodiments, the linkers thus selected can be:

1. Easily available;
2. Easy to link and cleave (please refer the probable protocols below); and/or
3. Not to interact with the polymerase and the polynucleic acid strand and/or not affect nucleotide polymerization and growth of a nascent nucleotide polymer.

The reporter moiety: In some embodiments, the reporter moieties can be associated with the other properties like the chromophoric nature for enabling their detection by UV or visible detector or the fluorescent nature making them to be detected by the fluorimetric detection.

The charge on the reporter: certain embodiments of the present invention describe the reporter moiety to carry a large charged mass. In one embodiment, the reporter moiety may introduce a higher charge mass to the synthetic nucleotide than the charge mass of the nucleotide or its derivative, which is present in the synthetic nucleotide. However, in another embodiment, the charge mass introduced by the reporter moiety can be substantially equal to or less than the charge mass of the nucleotide or its derivative, which is present in the synthetic nucleotide. Some non-limiting and illustrative examples of a reporter moiety are provided in this specification. These examples are provided only for the illustration purpose and therefore should not be considered to limit the scope of the invention. The chemical structure and/or dimension (e.g. length, size, and mass of a molecule used as a reporter moiety) of a reporter moiety may not be restricted as long as the reporter moiety is configured to provide a charge mass to the synthetic nucleotide and also not to affect polymerization reaction of nucleotides partially or entirely.

The charge on the moiety can be positive or negative. Taking into consideration the nature of linkage, the following provides some aspects of the selection of charge that can be possibly used in some embodiments of the present disclosure. In preferred embodiments, the charge is sufficient to cause a detectable change in a property (e.g., electrical resistance) of a sensitive detection nanostructure (e.g., a nanowire) which is operably coupled to the template sequence to which a synthetic nucleotide comprising the reporter moiety is added, e.g., during sequencing by synthesis.

Positive charge: In some embodiments, the large number of positive charges can generally be induced on the reporter moiety through the incorporation of tertiary amino groups on the aromatic or aliphatic skeleton. In such embodiments, in turn in the acidic pH (less than 7), these groups may acquire the positive charges making them detectable.

Negative charges: In some other embodiments, the negative charges can generally be induced on the reporter moiety through the incorporation of alcohol hydroxyl and/or phenolic hydroxy functionalities on the aromatic or aliphatic skeleton. Given below are some of the proposed reporter moieties which meet the above mentioned criteria. The fragments listed below may be available and able to link to the linker through the amino terminal. The additional advantage could be that the reagents that are proposed for the phosphoramidate linkage formation may be the same as this amide linkage formation (Therefore reducing costs of the system further).

Moreover, at least in part due to the stability of this linkage to the alkaline pH (above 7), the process of induction of negative charge would be of no or substantially small interference. For the purpose of illustration, the following three non-limiting examples are presented. These examples are provided only for the purpose of illustration and therefore should not be considered to limit the scope of the invention. As such, any modifications on the following examples are certainly included in the scope of the invention. For example, any substitution of one or more groups (e.g. —OH, ═O, COOH, and others) linked to the examples can be practiced. Also oligomerization or polymerization of one of more of the following examples can also be permitted. Further any other chemical structure or molecule with various dimensions (e.g. length, size, and mass of the reporter moiety) can be used as a reporter moiety if such chemical structure or molecule is configured to provide a charged mass to the synthetic nucleotide and also not to affect polymerization reaction of nucleotides partially or entirely.

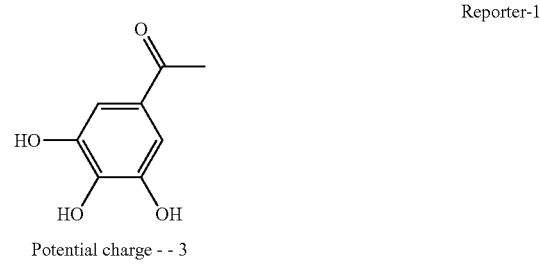

Reporter-1

Potential charge - - 3

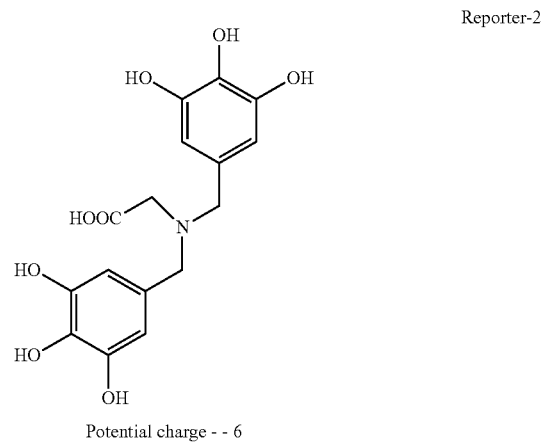

Reporter-2

Potential charge - - 6

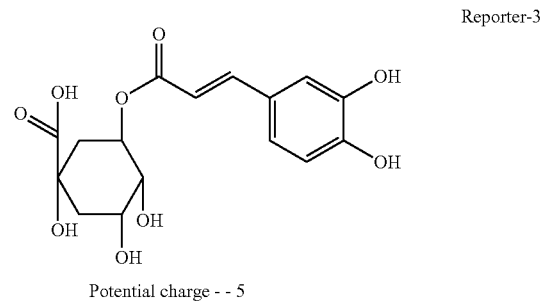

Reporter-3

Potential charge - - 5

After acquiring the charges, some of these reporters in certain embodiments may exist as follows,

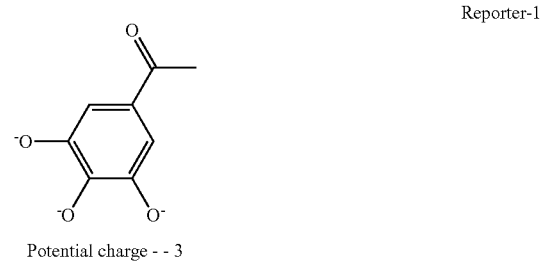

Reporter-1

Potential charge - - 3

Reporter-2

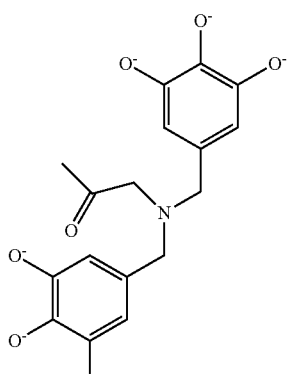

Potential charge - - 6

Reporter-3

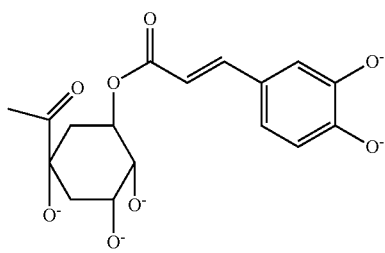

Potential charge - - 5

Whereas, the reporter-1 and reporter-3 may be available on shelf, reporter-2 may be custom synthesized.

The reporter moieties proposed can generally (be) thus:

1. Easily available or synthesizable;
2. bear a large charge;
3. Not costly; and/or
4. easy to link and cleave.

Final compounds (monomers): Based on the above propositions, the final structures of the nucleotides along with the linkers and the reporters would be as follows at least in certain parts of embodiments. The following examples of some final compounds are also provided for the purpose of illustration and therefore should not be considered to limit the scope of the invention. As described above, any variations permitted for a nucleotide or its derivative, a linker and a charge mass reporter moiety are also permitted to a final compound. Thus, for the adenosine as a nucleotide at the 5'-phosphate terminal in some examples, if the linker is, say, C13 equivalent (option 3 above), the various linkers would make the final structures looks as below:

One proposed final synthetic nucleotide-1 (note the reporter is in monomer form and this can be increased by aggregating these monomers to increase charge mass as required):

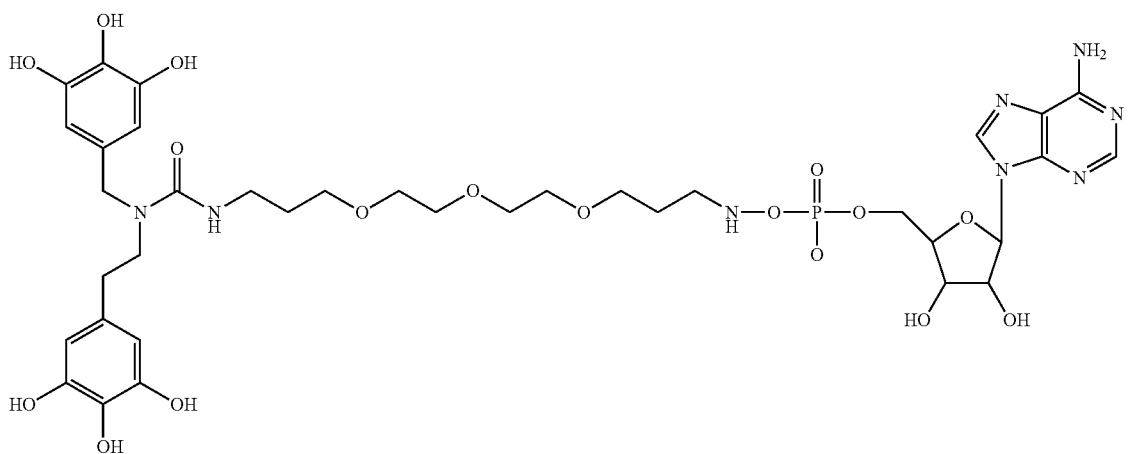 [SMILES: Nc1ncnc2c1ncn2C1OC(COP(=O)(O)ONCCCOCCOCCOCCCNC(=O)N(CCc2cc(O)c(O)c(O)c2)Cc2cc(O)c(O)c(O)c2)C(O)C1O]

Another proposed synthetic nucleotide-2 (note the reporter is in monomer form and this can be increased by aggregating these monomers to increase charge mass as required):

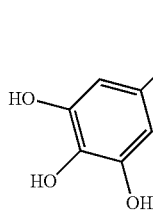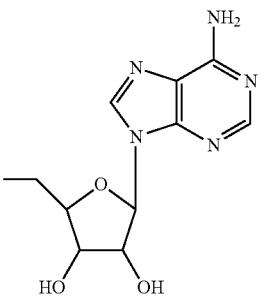

Still another proposed synthetic nucleotide-3 (note the reporter is in monomer form and this can be increased by aggregating these monomers to increase charge mass as required):

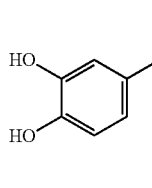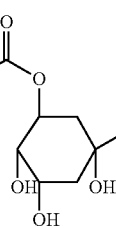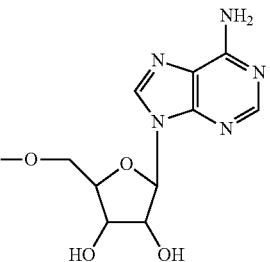

The following is a non-limiting, illustrative example of synthesis protocols used in at least some embodiments:

1. Synthesis of 5'-phosphoramidates of Adenosine: (Linkage of Nucleotide with the diamine linker). Method of Chu et all can be used for synthesizing 5'-amino derivatives of adenosine phosphoramidate in which diamantes and adenosine monophosphate (AMP) can be dissolved in water. EDAC was added later on and was incubated at room temperature with constant stirring. The reaction was monitored till completion.
2. Synthesis of Final proposed structures: (Linkage of the diamine linker with reporter moiety). Method of Chu et all can be used for synthesizing 5'-amino derivatives of adenosine phosphoramidate in which diamines and adenosine monophosphate (AMP) can be dissolved in water. EDAC was added later on and then incubated at room temperature with constant stirring. The reaction was monitored till completion.

One advantage of the similar procedure is that it may work out for both the steps leading to the formation of final compounds as monomers.

In some illustrative examples of some embodiments, (see below) cleavage of the linkers and reporter moieties may need to be done. The linkages like phosphoramidates can generally be rather readily cleaved by the use of acids like Trifluoroacetic acid at an ambient temperature.

By way of an illustrative example, the proposed synthetic nucleotide-2 demonstrated as a probable 3D view below. The aromatic ring at the bottom left of the molecule bears three hydroxy functions which could potentially get converted to the negative charge under slight alkaline conditions. Following is the 3D conformation of the Adenosine attached with the Reporter −1 through linker 3 and the related data.

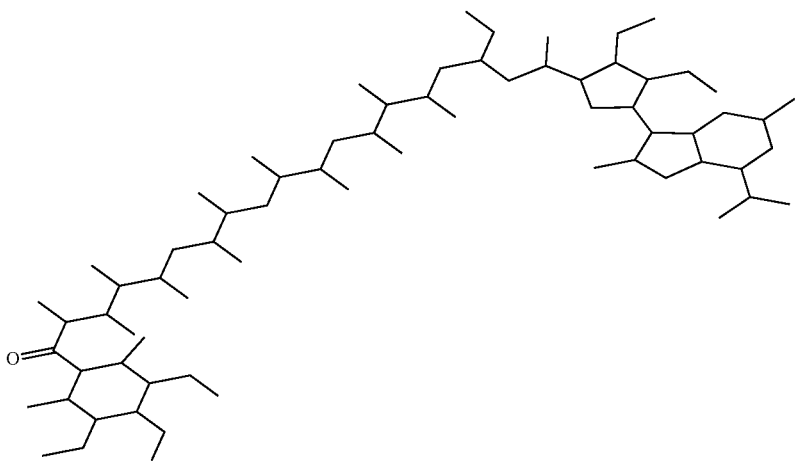 [SMILES: CCC(CC(C)C(C)C(C)CC(C)C(C)CC(C)C(C)CC(C)C(C)C(C)C(C)C(=O)C1C(C)C(CC)C(CC)C(CC)C1C)CC(C)C1CC(C2C(C)CC3C(C(C)C)CC(C)CC32)C(CC)C1CC]

Approximate distance between the phosphoramidate and terminal charged atom may be about 20 angstroms, which could generally be sufficient to induce the charge potential in the surface for detection. This distance can further be altered with the further modifications in the phase at least in part by changing the linker lengths. The charge on the terminal reporter moieties can also be changed by the variations in the chemistry of reporter moieties.

One aspect of the present disclosure describes a novel sequencing by synthesis technology. Sequencing by synthesis can be the general term used for determining the sequence of a single strand DNA molecule by growing the nascent, reverse compliment, strand and detecting the addition of each new nucleotide in the growing polymer. Using the more modern methods described above (methods employed by Helicos, 454 Life Sciences & Solexa), this can be performed by adding each separate nucleotide (adenine, guanine, cytosine or thymine) separately, in the presence of a polymerase and other elements required for polymerization, with a fluorescent reporter moiety ligated to the nucleotide and then observing the fluorescence using sensitive optical detection equipment. If there is fluorescence in the correct spectra for that nucleotide addition step, then the 'base calling' bioinformatic program may add the appropriate base in sequence. The reaction can then be washed and the next nucleotide in the cycle (wherein each of the four nucleotides Adenince, Guanine, cytoisine and Thyomine (or uracil for RNA) are added sequenntially) can be added. This cycle can be repeated until between approximately 25 bp to 900 bp or more (for example, depending on which method is used) worth of sequence data is obtained for each reaction (Reports from the market suggest read lengths of up to 900 bp are now possible using Roche's (ex 454) genome sequencer). To enable whole genome sequencing, many thousands of these reactions can be performed in parallel.

In some embodiments, the present sequencing methods and components can detect the addition of nucleotides by sensing their innate electrical charge, or the charge of a ligated 'high charge-mass' reporter moiety, using microfluidic chips, or reaction 'plates' arrayed with sensitive nanostructures that are capable of detecting a differences in charge densities at or near their surface (nanowire or nanotube FET biosensors, piezo-electric films, etc), or as molecules pass through them (nanopores), instead of using fluorescence and expensive optical detection equipment. Thus when a new nucleotide is added to the growing polymer in a sequencing by synthesis reaction the charge at, or near the surface (or through a nanopore) of the sensitive nanostructure may increase (due to the addition of the negative nucleotide and in some embodiments, the negative nucleotide and it's high charge-mass reporter moiety, being added) and this can be detected (for instance, if were to use a nanowire as the detecting structure, an increase in charge caused by the addition of a nucleotide close to its surface will be detected by a change in resistance in the wire, due to a phenomenon called the field effect) by a change in property in the sensitive detection nanostructure. However, as the polymer grows, the signal may diminish as the charges carried by the nucleotides being added may be too far away from the sensitive nanostructure (e.g. nanowire) to illicit a change in property of the sensitive detection nanostructure and no signal may be observed. Therefore, the 'read length' (amount of sequence data that is able to be obtained by this method of nucleotide sequencing) may be limited.

Some embodiments of the present disclosure address this limitation, at least in part by using synthetic nucleotides that comprise normal nucleotides, with a high negative charge mass reporter moiety attached via a linker molecule (for instance, attached to the 5' phosphate group, or the base group), with the linker length increasing as the reaction progresses. This high charge mass can generally be designed to 'reach down' to the sensitive nanostructure (e.g. nanowire) to cause a change in property of the sensitive detection nanostructure (e.g. a field effect or other piezo-electric change in the structure depending on the sensitive detection nanostructure used). To enable a good quality control measure and to ensure long read lengths by eliminating the build up of many reporter moieties which would cause an ever increasing field effect, these reporter moieties can be cleaved to allow for the addition of the next nucleotide in the sequencing by synthesis sequence. The cleavage of the reporter moiety effectively 'resets' the system allowing for clear signals and a more improved signal to noise ration than if using natural nucleotides without the linker plus high charge-mass reporter moiety.

Therefore, in some embodiments, the cyclical reaction comprises at least some or all of the following series of events:
1. The template molecule (DNA, RNA, or other synthetic nucleotide polymer molecule such as PNA or morpholino oligos) to be sequenced can either be ligated to the sensitive detection nanostructure and a primer added, bind to a pre-immobilized primer sequence on the sensitive detection nanostructure, or uncoiled and elongated in a microfluidics channel arrayed with sensitive detection nanostructures;
2. The sensitive detection nanostructures can be washed with water, or a low salt buffer (such as 1×SSC);
3. A measure of the sensitive detection nanostructure can be made (baseline measurement);
4. A mixture containing one synthetic nucleotide, the polymerase and other elements required for the polymerisation reaction can be added. If the nucleotide added is complimentary to the base on the template molecule immediately after the primer sequence, it may be incorporated into the growing 'nascent' chain by the polymerase;
5. The reaction can then be washed, for instance with either water or a low salt buffer (such as, but not limited too, 1×SSC);
6. A measure of the sensitive detection nanostructure may be made which may observe the effect caused by the high charge mass of the reporter moiety (intermediate measurement);
7. The reporter moiety can then be cleaved (for instance by an acid solution or enzymatically)
8. The reaction can then be washed, for instance with either water or a low salt buffer (such as, but not limited to, 1×SSC);
9. A measurement of the sensitive detection nanostructure may be made which may observe the effect of just the added nucleotide without the linker and high charge mass reporter moiety (Baseline+1 measurement); and/or
10. Points 2 through 9 may be repeated for each of the four nucleotides. And this can be repeated repeatedly until a clear signal degrades.

For some embodiments wherein the template molecule is immobilized to, or bound to a probe that can be in turn immobilized to the sensitive detection nanostructure, the linker lengths that attach the high charge reporter moiety to the synthetic nucleotides may increase to enable the charge to 'reach down' to the sensitive detection nanostructure to exert an effect. This may be necessary at least in some embodiments as the growing nucleotide polymer may move the next nucleotide addition site farther and farther from the sensitive detection nanostructure as the sequencing by synthesis reaction progresses. By increasing the length of the linker lengths as the reaction continues, the charge mass reporter moiety will still 'reach down' to the sensitive detection nanostructure to illicit change, even though the addition of the nucleotides is further from the sensitive detection nanostructure than would normally allow a signal, as the nascent chain grows.

For some other embodiments wherein the template molecules is not immobilized to the sensitive detection nanostructure, or hybridized to a primer/probe that can be in turn immobilized to the sensitive detection nanostructure, and can be instead free or immobilized horizontally across a cluster of sensitive detection nanostructures, a single linker length can be used for each of the cycle reactions.

Some aspects of embodiments of the present disclosure describe a method of sequencing nucleotide polymers (DNA or RNA) by incorporating synthetic nucleotides, ligated, via a linker molecule to a reporter moiety, in a 'sequencing by synthesis' reaction. As used herein in various embodiments, 'sequencing by synthesis' generally describes a method of nucleotide sequencing wherein the addition of each nucleotide to the nascent chain (i.e. the growing nucleotide polymer, reverse compliment to the template nucleotide polymer) can be detected in real time. Some other embodiments, rather than detecting nucleotide monomer additions to the nascent chain by using the traditional optical detection of fluorescent labels (as used in presently available sequencing by synthesis techniques), can detect each nucleotide addition based upon the charge mass of the nucleotide monomer. In some other embodiments, the charge mass of a covalently ligated charge mass reporter moiety, using a sensitive detection nanostructure, or other structure capable of detection minute may change in surface charges.

As used herein in some aspects of embodiments, a "sensitive detection nanostructure" can generally be any structure (nanoscale or not) capable of generating a signal in response to a change in a property of the nanostructure within an assay region. As used herein an "assay region" refers generally to the area or region in which the nanostructure or nanostructures at least partially reside, and in which the nanostructure(s) is operably coupled to a biomolecule (nucleic acid, primer, target sequence, etc.) e.g., via a direct or indirect bond or linkage, covalent or not, or just in close enough physical proximity to exhibit a change in property and generate a signal in response to a change in the biomolecule. In preferred embodiments, such a change in property may be caused by a change in charge of a biological molecule operably coupled to the nanostructure within the assay region. Typically, the nanostructure is sensitive to changes at or near its surface (such as with nanowire or carbon nanotube FET biosensors), or as molecules pass through it (such as nanopore biosensors)—although the assay region may extend beyond the surface of the nanostructure to include the entire region within the field of sensitivity of the nanostructure. The nanostructure is preferably also coupled to a detector that is configured to measure the signal and provide an output related to the measured signal. At any point along the length of the nanostructure, it may have at least one cross-sectional dimension less than about 500 nanometers, typically less than about 200 nanometers, more typically less than about 150 nanometers, still more typically less than about 100 nanometers, still more typically less than about 50 nanometers, even more typically less than about 20 nanometers, still more typically less than about 10 nanometers, and even less than about 5 nanometers. In other embodiments, at least one of the cross-sectional dimensions can be less than about 2 nanometers, or about 1 nanometer. In one set of embodiments the sensitive detection nanostructure can be at least one cross-sectional dimension ranging from about 0.5 nanometers to about 200 nanometers.

As used in various embodiments, a nanowire is an elongated nanoscale semiconductor which, at any point along its length, has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. In other embodiments, the cross-sectional dimension can be less than 2 nanometers or 1 nanometer. In one set of embodiments the nanowire has at least one cross-sectional dimension ranging from 0.5 nanometers to 200 nanometers. Where nanowires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below. Nanotubes are a class of nanowires that find use in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself. Preferred electrically conductive materials have a resistivity lower than about $10^{-3}$, more preferably lower than about $10^{-4}$, and most preferably lower than about $10^{-6}$ or $10^{-7}$ ohm-meters.

Nanopore generally has one or more small holes in an electrically insulating membrane. Nanopore is generally a spherical structure in a nanoscale size with one or more pores therein. According to some aspects, a nanopore is made of carbon or any conducting material.

Nanobead is generally a spherical structure in a nanoscale size. The shape of nanobead is generally spherical but can also be circular, square, rectangular, elliptical and tubular. Regular and irregular shapes are included. In some examples, the nanobead may have a pore inside.

Nanogap is generally used in a biosensor that consists of separation between two contacts in the nanometer range. It senses when a target molecule, or a number of target molecules hybridize or binds between the two contacts allowing for the electrical signal to be transmitted through the molecules.

The foregoing nanostructures, namely, nanowire, nanotube, nanopore, nanobead, and nanogap are described to provide the instant illustration of some embodiments, and not for limiting the scope of the present invention. In addition to the foregoing examples, any nanostructure that has a nanoscale size and is suitable to be applied to nucleic acid sequencing methods and apparatus as disclosed in the application should also be considered to be included in the scope of the invention.

In general, nucleotide sequencing strategies for use with nanostructures or nanosensors is to sense the charge at, or near the surfaces, or across a nanogap or nanopore, which cause a measurable change in their properties (such as field effect transistors, nanogaps, or piezoelectric nanosensors). The charge sensed by the nanostructure can be originated from the nucleotide complementary to the template nucleotide that is added during the sequencing reaction. In some embodiments, the complementary nucleotide added during the sequencing reaction is linked to a linker and a high charge mass reporter moiety, which are described in detail elsewhere in the specification.

Field effect generally refers to an experimentally observable effect symbolized by F (on reaction rates, etc.) of intramolecular coulombic interaction between the centre of interest and a remote unipole or dipole, by direct action through space rather than through bonds. The magnitude of the field effect (or 'direct effect') may depend on the unipolar charge/dipole moment, orientation of dipole, shortest distance between the centre of interest and the remote unipole or dipole, and on the effective dielectric constant. This is exploited in transistors for computers and more recently in DNA field-effect transistors used as nanosensors.

Field-effect transistor (FET) is generally a field-effect transistor, which may use the field-effect due to the partial charges of biomolecules to function as a biosensor. The structure of FETs can be similar to that of metal-oxide-semiconductor field-effect transistor (MOSFETs) with the exception of the gate structure which, in biosensor FETs, may be replaced by a layer of immobilized probe molecules which act as surface receptors.

In some embodiments, the sequencing reaction may begin by hybridizing a short 'probe' or 'primer' nucleic acid molecule, often referred to as an oligonucleotide, wherein a 'probe' or 'primer' can generally be a single stranded nucleotide polymer molecule, ssDNA, RNA, PNA, Morpholino, or other synthetic nucleotide, to the 5' end of the 'target' nucleotide molecule, wherein the 'target' molecule can generally be the nucleotide polymer of interest. It is the nucleotide sequence of this single stranded nucleotide polymer molecule, ssDNA or RNA that can be to be determined. Furthermore, the 'probe' or 'primer' sequence can generally be reverse complimentary to the 'target' nucleic acid molecule to be sequenced and sufficiently long to facilitate hybridization-primer design is well known to those skilled in the art and many commercial and freeware software platforms are available to facilitate primer, or probe design.

In some embodiments, short adaptamers (another short oligonucleotide of known sequence) can generally be ligated to the target nucleotide polymer and the primer or probe can be designed to be reverse compliment to this oligonucleotide sequence. In some embodiments the primer or probe molecule can be immobilized on a sensitive detection nanostructure and the target nucleotide molecule can be hybridized to the primer. In other embodiments, the target molecule can be first immobilized to the sensitive detection nanostructure and primers or probes can be hybridized. In yet another embodiment, both the target nucleotide molecule and the primer and probe molecules may be free and not immobilized, but positioned close to the sensitive detection nanostructures, and at least in some embodiments the hybridized target and primer or probe molecules may be sufficiently close to exert a measurable change in properties in the sensitive detection nanostructure. This might be by positioning the molecules in a microfluidics environment, or other undefined methodologies. The following is a non-limiting, illustrative example of certain embodiments of the present disclosure. In one example, the first step in the technique can be to take a series of measurements (for instance a measure of resistance in a nanowire or other field effect transistor) of the sensitive detection nanostructure in air, the presence of water, or a low salt buffer (such as 1×SSC). This can provide the base level for the property of the sensitive detection nanostructure that can be to be measured in response to ongoing reaction (e.g. the electrical resistance in a nanowire). The sequencing by synthesis reactions can be initiated by adding a single nucleotide species (along with a polymerase and other chemicals required for polymerization), such as Adenine to the reaction. As all nucleotides may posses a natural charge, following the addition of the Adenine in the nascent chain (assuming the next nucleotide in the target nucleotide polymer is a Thymine) the charge at, or close to, a sensitive detection nanostructure, created by this extra Adenine in the nascent chain, may cause a measurable change in properties in the sensitive detection nanostructure, which may be recorded, following a wash step to eliminate background noise from the high ionic PCR reaction mix.

Therefore, in certain examples, if there is a Thymine (or Uracil if sequencing RNA) nucleotide next in the template nucleotide, then once Adenine can be added to the sequencing by synthesis reaction, it can be incorporated in the nascent chain, by the polymerase (which can also be added as part of the reaction) and a signal detected, at least in part due to the change in electrical charge at, or near the surface of the sensitive nanostructure, caused by the extra nucleotide in the nascent chain. However, should either Cytosine, Guanine, or Thymine been added instead, then no nucleotide would have been added to the nascent chain and no change in signal would have been observed from the sensitive nanostructure.

In certain other embodiments, each nucleotide can be added, one after the other, to the reaction mix, with polymerase and $MgCl_2$, $H_2O$ and buffer to enable polymerization of a complimentary nucleotide addition to the target sequence in the nascent chain. After each nucleotide addition, the reaction can be washed and the next nucleotide added. This cycle can be repeated for all four nucleotides. Once all four nucleotides can be added, the cycle can be repeated until the desired sequence may be elucidated, or the signal may deteriorate.

In various embodiments, the synthetic nucleotides may comprise one or more of nucleotides, Adenine, Guanine, Cytosine & Thymine, plus isoforms of these bases (such as Inosine) with a reporter moiety attached, for instance, via a linker to the 5' phosphate group. If the sensitive detection nanostructure may not be sensitive enough to detect changes cause by single nucleotides, some embodiments of the present disclosure describes the use of synthetic nucleotides that comprise nucleotides with a charge mass reporter molecule ligated to the nucleotide via a long linker molecule, sufficiently long enough to ensure that the reporter may not have a significant deleterious effect on polymerase activity. The linker molecules can vary in length, and enable the reporter moiety to extend out from the DNA Polymerase complex so that polymerization (nucleotide addition) may not be prevented, or unduly hindered. Furthermore, as the sequencing by synthesis reaction progresses, the nucleotides added to the nascent chain can get further and further from the sensitive detection nanostructure, which may diminish the signal. To combat this and to therefore provide longer read lengths, the linker molecule lengths can be increased to enable the reporter charge mass moieties to 'reach down' to the sensitive detection structures to provide a clear signal.

In some embodiments, as each nucleotide can be added to the nascent chain, the reporter moieties can build up and would eventually overload the sensitive detection structures at least in part due to their aggregating charges. To combat this, in certain illustrative examples, some embodiments may assume that the charges can be cleaved, whether by enzymatic, chemical, light, or other methods, after each nucleotide can be added and the signal in the sensitive reporter moiety recorded. Once the linker and the reporter moiety can be cleaved and washed away, another measurement in the sensitive detection structure can be taken to serve as a quality control, or to 'reset' the system to improve the signal to noise ration, before the next nucleotide can be added to the reaction.

Homopolymer stretches may have a problem for fluorescence based sequencing technologies, as a dinucleotide stretch may provide twice the intensity of fluorescence and the trinucleotide may stretch three times the intensity of fluorescence, and so on. This may cause significant difficulties in interpretation and base calling.

Much like the some fluorescence based sequencing technologies, various embodiments used in connection with the present disclosure can generally differentiate between di-, tri-, etc homopolymer stretches by measuring the intensity of the signal (this can be possible if the sensitive detection nanostructure can be capable of quantitative or semi-quantitative measurements, such as some nanowire or carbon nanotube FET biosensors are).

Alternatively, if the sensitive detection nanostructure may not be able to differentiate between dinucleotide, tri-nucleotide and other homopolymer additions, some embodiments may use synthetic nucleotides designed to allow the addition of one nucleotide and therefore prevent the addition of other nucleotides. One illustrative method to achieve this can be to link the reporter moiety to the 5' phosphate group, which may prevent further nucleotide additions to the nascent chain. Once the reporter and linker are cleaved, the next nucleotide can be added. Another illustrative method can be to place a cleavable cap molecule at the 5' phosphate to prevent further nucleotide additions to the nascent chain, with the linker and reporter moiety linked to another site on the nucleotide. Cap removal may then allow for the next nucleotide to be added and the process repeated.

In some embodiments of this disclosure, all nucleotides can be added to the reaction mix, for example, at the same time, however each of the synthetic nucleotides may have a different distinct charge mass reporter moiety, at least in some embodiments. Measurements of the sensitive detection nanostructures can be taken about every 2-3 ms, to mimic the speed at which polymerase may add nucleotides to the nascent chain, which can be estimated at about 3 ms at a temperature of about 65° C. In such embodiment, the reporter moieties may not be cleaved, so the read lengths may be shorter at least in part due to the signal to noise ratio decreasing as the nascent chain may extend and charge reporter moieties can build up, but sequencing time can be much quicker. In certain embodiments, a synthetic polymerase, that can be engineered to catalyze the polymerization reaction slower.

EXAMPLES

The followings are some illustrative and non-limiting examples of some embodiments of the present disclosure.

Example 1—DNA Sequencing

The sequencing methodology in one example may not use fluorescence and expensive sensitive cameras, but instead may detect the addition of the synthetic nucleotides described in some aspects of the present disclosure, at least in part by sensing the electrical charge of reporter moiety, using sensitive nanostructures that may be capable of detecting a build up of charge mass within the assay region, e.g., at or near the surface of the sensitive detection nanostructure. When a new nucleotide is added to the growing polymer in a sequencing by synthesis reaction, the charge density at, or near the surface of the sensitive nanostructure may increase and this can be detected by a change in property in the sensitive detection nanostructure (for instance, if using a nanowire, or carbon nanotube, as the detecting structure, an increase in charge caused by the addition of a nucleotide close to its surface may be detected by a change in resistance in the wire, due to a phenomenon called the field effect). However, as the polymer grows, the signal may diminish as the charges carried by the nucleotides being added may be too far away from the sensitive nanostructure (e.g. nanowire) to illicit a change in property of the sensitive detection nanostructure and no signal may be observed. Therefore, the 'read length' (amount of sequence data that is able to be obtained by this method of nucleotide sequencing) can be limited.

As used herein this particular example, a "sensitive detection nanostructure" can be any structure (nanoscale or not) which can be capable of detecting any change in charge at, or near it's surface and at any point may have at least one cross-sectional dimension less than about 500 nanometers, typically less than about 200 nanometers, more typically less than about 150 nanometers, still more typically less than about 100 nanometers, still more typically less than about 50 nanometers, even more typically less than about 20 nanometers, still more typically less than about 10 nanometers, and even less than about 5 nanometers. In other embodiments, at least on of the cross-sectional dimensions can generally be less than about 2 nanometers, or about 1 nanometer. In one set of embodiments the sensitive detection nanostructure can have at least one cross-sectional dimension ranging from about 0.5 nanometers to about 200 nanometers.

The properties of a sensitive detection nanostructure may change in response to surface, or near surface charge in a way that may be measurable via piezoelectric measurements, electrochemical measurement, electromagnetic measurement, photodetection, mechanical, measurement, acoustic measurement, gravimetric measurement and the like. An example of a sensitive detection nanostructure may include, but not limited to, two dimension field effect transistors, a cantalevers, nanowires, carbon nanotubes, and all piezoelectric macro-, micro-, nano-, pico-, zempto-, or smaller structures.

Certain embodiments of the present disclosure may address this limitation, at least in part by using synthetic nucleotides that may comprise normal nucleotides, with a high negative (or positive) charge mass reporter moiety attached via a linker molecule (for instance, attached to the 5' phosphate group), with the linker length increasing as the reaction progresses. This high charge mass can be designed to 'reach down' to the sensitive nanostructure (e.g. nanowire) to cause a change in property of the sensitive detection nanostructure (e.g. a field effect or other piezoelectric change in the structure depending on the sensitive detection nanostructure used). To enable a good quality control measure and to ensure long read lengths by eliminating the build up of many reporter moieties which would cause an ever increasing field effect, these reporter moieties can be cleaved at least in certain embodiments, to allow for the addition of the next nucleotide in the sequencing by synthesis sequence.

Therefore, in some embodiments the cyclical reaction may comprise at least some or whole of the following entire or partial series of events:
1. The template ssDNA molecule to be sequenced can be either ligated to the sensitive detection nanostructure and a primer added, bind to a pre-immobilized primer sequence on the sensitive detection nanostructure, or uncoiled and elongated in a microfluidics channel arrayed with sensitive detection nanostructures.
2. The sensitive detection nanostructures can be washed with water, or a low salt buffer (such as 1×SSC). This washing, however, may not be necessary in some embodiments.
3. A measure of the sensitive detection nanostructure can be made.
4. A mixture containing one synthetic nucleotide, the polymerase and other elements required for the polymerization reaction can be added. In one example, if the nucleotide added is complimentary to the base on the minus strand immediately after the primer sequence, it maybe incorporated into the growing chain by the polymerase.
5. The reaction can then be washed with either water or a low salt buffer (such as 1×SSC). This washing, however, may not be necessary in some embodiments.
6. A measure of the sensitive detection nanostructure can be made which can observe the effect caused by the high charge mass of the reporter moiety.
7. The reporter moiety can then be cleaved (for instance by an acid solution or enzymatically). This cleavage of reporter moiety, however, may not be necessary in some embodiments.
8. Points 2 through 7 can be repeated for each of the four nucleotides. And this can be repeated repeatedly until a clear signal may degrade.

For some embodiments wherein the template molecule is immobilized to, or bound to a probe that can be in turn immobilized to the sensitive detection nanostructure, the linker lengths that attach the high charge reporter moiety to the synthetic nucleotides may increase to enable the charge to 'reach down' to the sensitive detection nanostructure to exert an effect. This may be necessary at least in some embodiments as the growing nucleotide polymer may move the next nucleotide addition site farther and farther from the sensitive detection nanostructure as the sequencing by synthesis reaction may progress.

For some other embodiments wherein the template molecules is not immobilized to the sensitive detection nanostructure, or hybridized to a primer/probe that can be in turn immobilized to the sensitive detection nanostructure, and can be instead free or immobilized horizontally across a cluster of sensitive detection nanostructures, a single linker length can be used for each of the cycle reactions Example 2—Parallel Polony Sequencing In one embodiment, genomic DNA may be fragmented by methods known to those skilled in the art (such as sonication, restriction enzyme digestion, etc). Adaptamers (a short synthetic oligo nucleotide-DNA, or other synthetic oligonucleotide) can be then ligated to the fragments, an A adaptamer ligated to the 5' end and a B adaptamer ligated to the 3' end.

The A adaptamer may contain a restriction enzyme binding site and the B adaptamer may be complimentary to another oligonucleotide immobilized to a nanostructure, such as a nanosphere. This oligonucleotide can be DNA, or any other synthetic nucleic acid and can generally be immobilized with methods familiar to those skilled in the art (for instance using a streptavidin coating on the nanostructure and biotin ligated to the terminal nucleotide in the oligonucleotide chain). These nanostructures can generally be added to the library of small genomic fragments, with ligated A & B adaptamers, in excess and then the whole mixture, with PCR reagents added, emulsified in oil, so that tiny microreactors of nanostructure plus a single strand of the fragmented genome may allow for huge multiplex amplification of the genome using the polymerase chain reaction. As the nanostructures can be added in excess, the dilution can be such that only one fragment may bind to anyone nanostructure. The amplified fragments, within each microreactor may naturally bind to the nanostructures, as they are synthesised, which can be coated in DNA (or another synthetic nucleotide, such as PNA, morpholinos, etc), complimentary to the B adaptamers. Thus each microreactor, following the polymerase chain reaction, may comprise a nanostructure coated in a single species of amplified genomic fragment in certain parts of embodiments.

In some instances, these nanostructures, coated with a single species of amplified genomic fragment can then be added to a special pico-titre plate, which may comprise hundreds of thousands of reaction wells. At the base of each well can be an array of individually addressed sensitive detection nanostructures coated with a 'primer', or 'probe' oligonucleotide complimentary to the A adaptamer. The wells can be of such a size to allow only one nanostructure in certain cases, coated in an amplified genomic fragment to rest in it. Once these nanostructures can be allowed to rest in the pico-wells, the reaction plate can be washed with a low salt buffer (such as 1×SSC).

In one embodiment, a measure of the sensitive detection nanostructure resistance can be taken as the baseline signal. Polymerase (the enzyme that can read the DNA and add complimentary bases) may be added, with a single nucleotide (either Adenine Guanine, Cytosine or Thymine) and chemicals (such as $MgCl_2$) required for polymerase activity, can be added and the sequencing by synthesis reaction can be performed, as described above, in parallel, in each well of the pico-titre plate.

In some embodiments, synthetic nucleotides, which have a charge moiety added—as described above—can be used to amplify the signal. Furthermore, as the sequencing by synthesis reaction progresses and the next nucleotide to be added to the nascent chain gets further from the sensitive detection nanostructure, the length of the linker molecules can be increased to 'reach-down' to induce a signal in the sensitive detection nanostructure from afar, thus enabling longer read lengths.

In other embodiments, following the wash step, a restriction digest can be performed with the restriction enzyme cutting at the site in the A adaptamer. This may release the nanostructure, which may be washed away. The sequencing by synthesis reaction can then be performed, as above, but without the presence of the nanostructure in the pico-well.

Example 3—Long Read-Length Sequencing in Microfluidics Channels or Flow Cells

In some embodiments, target DNA sequences can be sequenced in a microfluidics channel arrayed with sensitive detection nanostructures.

The genomic, or other nucleotide polymer molecule sample can be fragmented into fragments > about 1 kb, but under about 10 kb and can have an adaptamer (reverse compliment to the sequencing primer) ligated to the 5' end. These fragments can be then positioned within a microfluidics channel, one per channel, either by hybridizing the 5' adaptamer sequence to an immobilized probe at the mouth of the microfluidics channel and flowing a low salt buffer through the channel to draw the nucleotide polymer fragment into the channel, or by allowing the nucleotide polymer to naturally diffuse and uncoil into the microfluidics channel, or another method.

In such embodiment, once the nucleotide polymer fragment can be in the microfluidics channel the sequencing by synthesis reaction can begin, with each arrayed sensitive nanostructure taking a measurement. Not only may these sensitive nanostructures detect the additions of bases, but as the nascent chain may extend the spatial positions of each base addition can be determined as each subsequent sensitive detection nanostructure may begin to detect a signal, and those upstream may stop detecting a signal.

One of key aspects of such embodiments can be to ensure the surface chemistry within the microfluidics channel prevents binding and aggregation of the charged reporter moieties or unincorporated nucleotides, as these may cause background noise.

Example 4—Handheld Sequencing Device

In some embodiment, specific target DNA sequences may be sequenced in a microfluidics channel arrayed with sensitive detection nanostructures as above. However, the sequencing by synthesis reagents can be stored in a microfluidics channel, each nucleotide mix, wash solution and charge reporter moiety cleavage buffer, separated by an air bubble, or another method of separating the reagents.

In some embodiment, small specific regions of target viral, bacterial or genomic DNA can be to be sequenced to be diagnostic for the presence or absence of a specific virus, bacteria, or sequence (such as a SNP).

Various embodiments used in connection with the present disclosure lend itself to handheld sequencing as it may not require bulky and expensive cameras or lasers to detect the sequencing reaction. Furthermore, by placing the reagents one after the other in sequence, they may be easily manipulated within a microfluidics environment.

The following figures are presented to provide some illustrative and non-limiting examples of various embodiments, FIG. 1 A. In one embodiment, a probe sequence can be immobilized on a sensitive detection nanostructure (in this case a nanowire) and the template ssDNA molecule to be sequenced can hybridize to the probe sequence and the probe sequence can act as a primer for the sequencing by synthesis reaction. B. In this embodiment the template ssDNA molecule can be immobilized to the sensitive detection nanostructure and can be primed for sequencing with a free primer oligonucleotide.

In such embodiments, once the target DNA is bound to the immobilized primer/probe, or the primer hybridizes to the immobilized target DNA, a measurement can be taken from the sensitive detection (for instance, in a nanowire or carbon nanotube, a resistance reading is taken).

Figure 2:
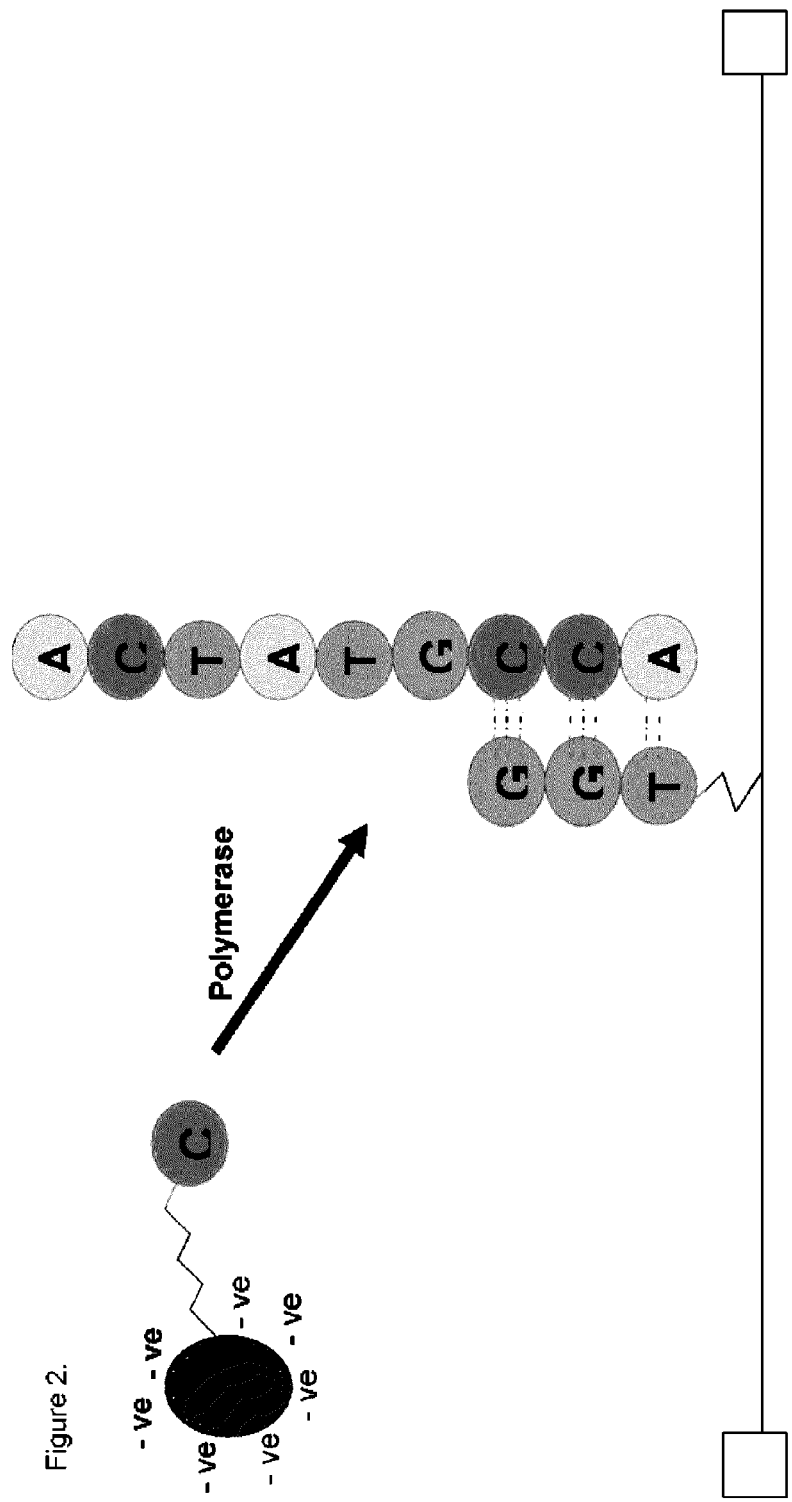
FIG. 2 is a depiction of an illustrative embodiment of some part of the sequencing by synthesis reaction.

FIG. 2 illustrates the next step in the sequencing by synthesis reaction in some embodiments, wherein a solution comprising at least some of a single species of synthetic nucleotides, polymerase and chemical required for polymerization can be added.

Figure 3:
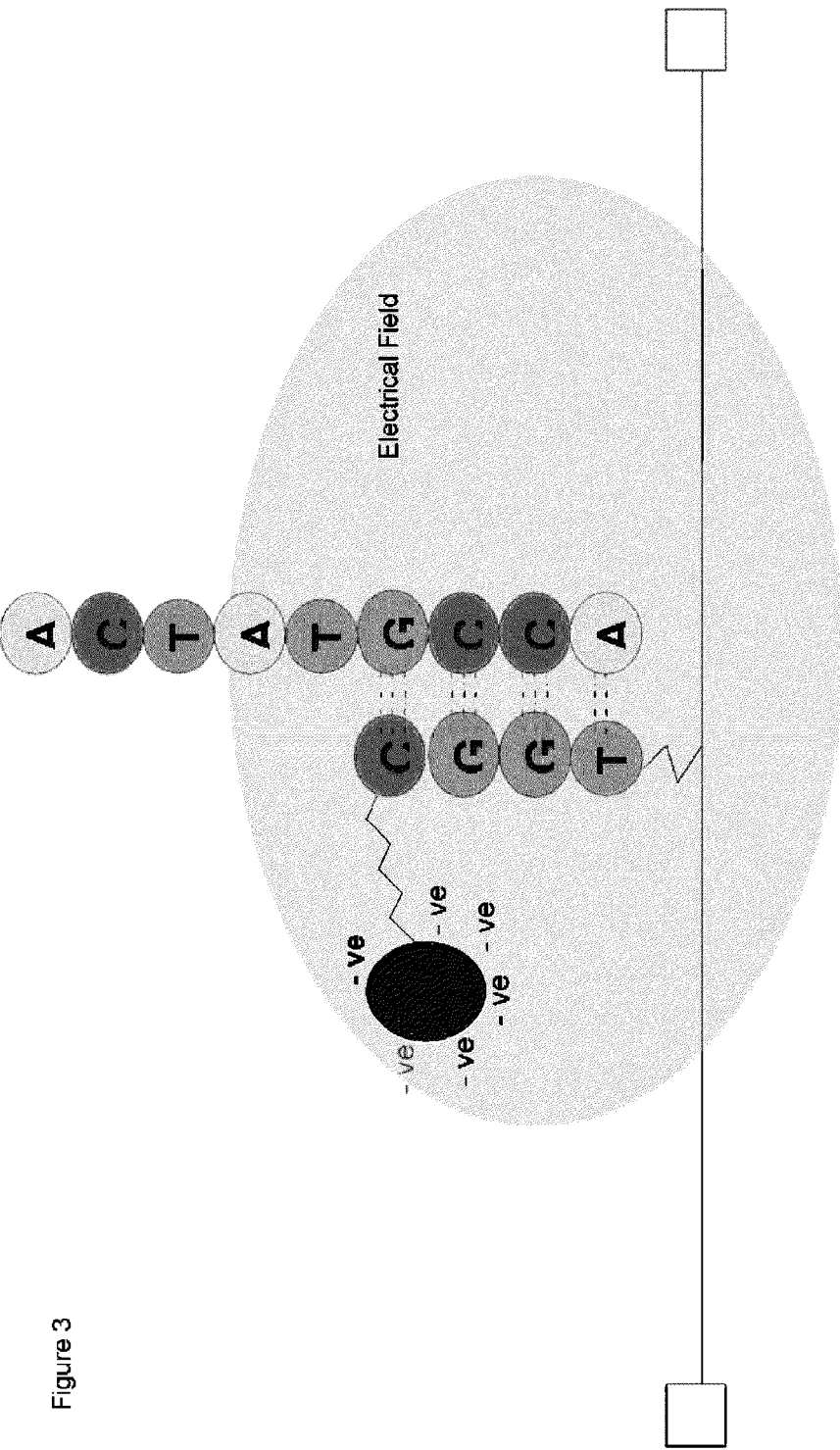
FIG. 3 is a depiction of an illustrative embodiment of the addition of a synthetic nucleotide base to the nascent chain.

FIG. 3 illustrates the addition of a synthetic nucleotide base to the nascent chain in some embodiments. The ligated high negative charge mass reporter moiety can extend from the synthetic nucleotide sequence and 'reaches-down' to cause a measurable change in properties in the sensitive detection nanostructure (in this case a field effect in a nanowire).

A second measurement of the sensitive detection nanostructure can be taken at this point.

Figure 4:
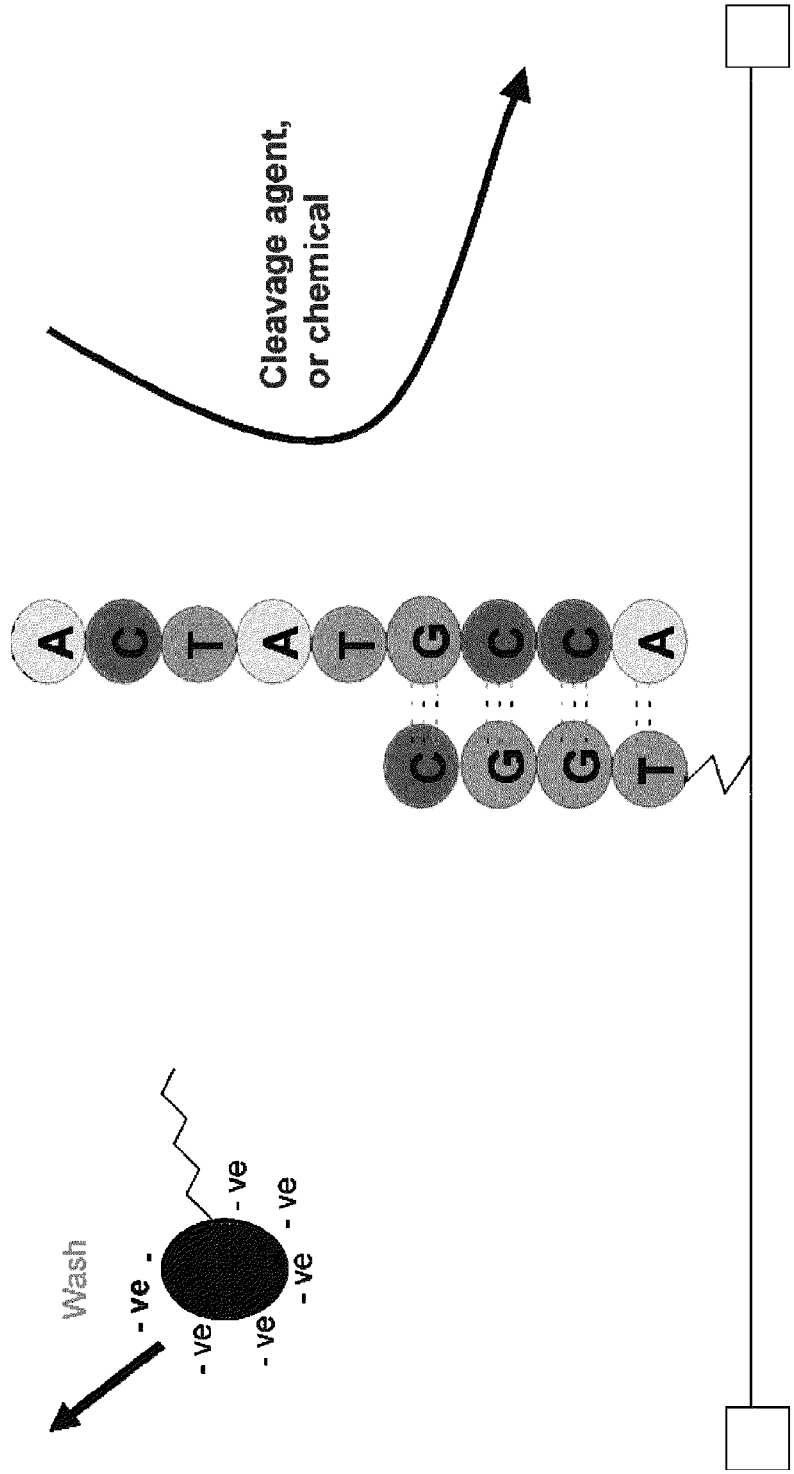
FIG. 4 provides an illustration of some embodiments of the cleavage of the linker and high charge mass reporter moiety ligated to the nucleotide.

FIG. 4 illustrates the linker and high charge mass reporter moiety ligated to the added nucleotide can be cleaved, either enzymatically, with an acid, or other chemical or method, and washed away in some embodiments.

A third measurement of the sensitive detection nanostructure can be taken at this point.

The cycle of FIG. 2 through 4 can be repeated for the other three nucleotides and then again repetitively for all four until the desired sequence can be obtained or the signal degrades.

Figure 5:
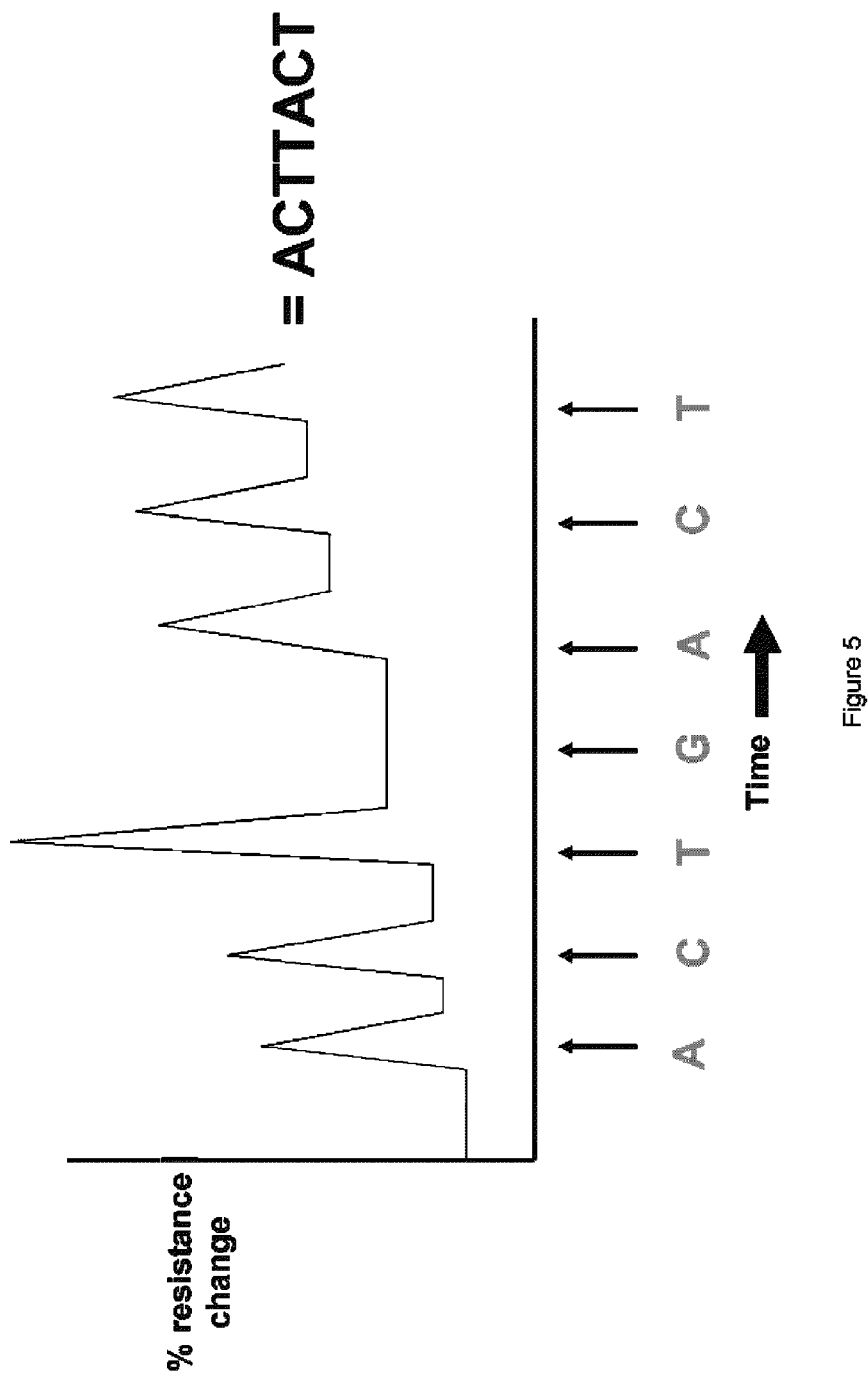
FIG. 5 illustrates a depiction of the possible results from the measurements from the sensitive detection nanostructures in some embodiments.

FIG. 5 illustrates a depiction of the results from the measurements from the sensitive detection nanostructures after seven cycles consisting following the following nucleotide additions Adenine, Cytosine, Thymine, Guanine, Adenine, Cytosine, and finally Thymine in some embodiments. The first and second cycles that may cause a change in properties of the sensitive detection nanostructure, which can be interpreted as CT as the first two base pairs in the nascent strand. The third cycle that may provide a large signal, twice the order of magnitude that of the first two cycles (this may be possible if the sensitive detection nanostructure can be capable of quantitative or semi-quantitative measurements to differentiate between a dinucleotide stretch, tri-nucleotide stretch and other homopolymer stretches).

Alternatively, in some other embodiments, if the sensitive detection nanostructure can be not able to differentiate between di-nucleotide, tri-nucleotide and other homopolymer additions, the synthetic nucleotides can be designed to allow the addition of, in one example, only one nucleotide and therefore may prevent the addition of other nucleotides. Upon cleavage of the linker and reporter moiety the ability to add further nucleotides to the nascent chain can be restored. Therefore, at least in this example the sequence from this cycle would result in ACTT only.

Figure 6:
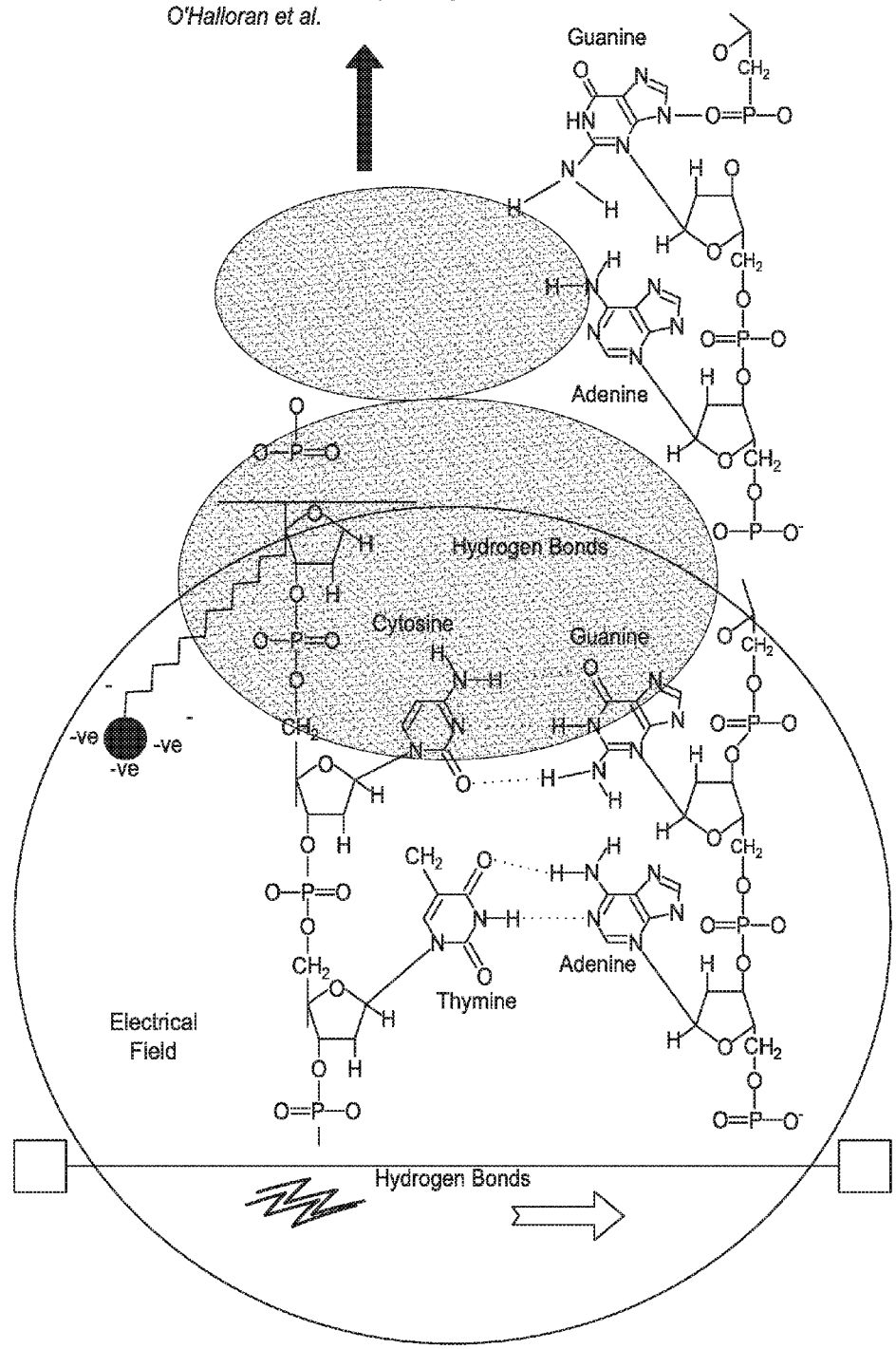
FIG. 6 illustrates an example of a polymerase complex.

FIG. 6 illustrates a polymerase complex adding a synthetic nucleotide base to the nascent chain as part of the polymerization reaction in some embodiments. Note the linker molecule protrudes out from the polymerase complex in this particular example, therefore not deleteriously affecting its action, and 'reaches-down' to the sensitive detection nanostructure (in this case a nanowire or carbon nanotube) to exert its effect on the structure which can in turn be measured and recorded following washing away the polymerase complex and chemicals required to enable it to work. Once the measurement can be taken the linker and reporter moiety can be removed and another measurement (baseline+1 nucleotide) can be taken, before the next nucleotide in the sequencing by synthesis reaction may be added.

Figure 7:
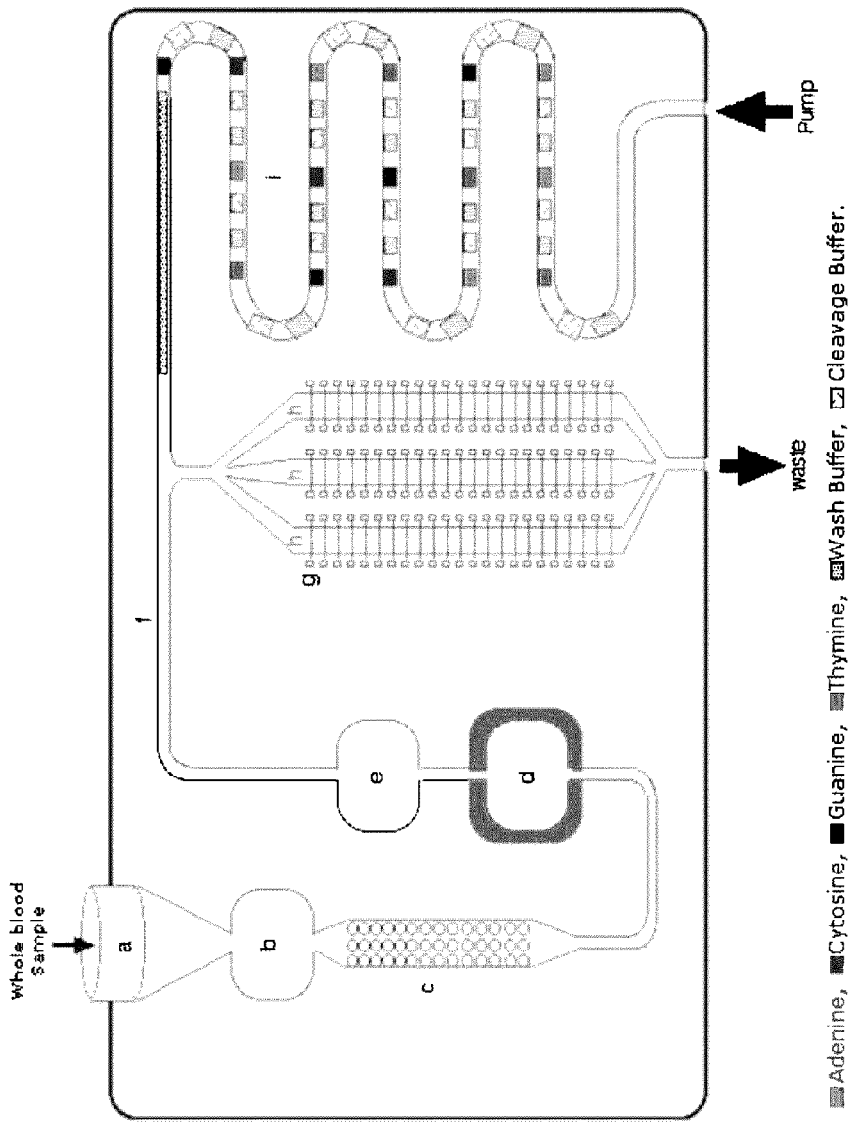
FIG. 7 illustrates an example of microfluidics cassette designs for handheld sequencing in some embodiments.

FIG. 7 illustrates a microfluidics cassette design designed for handheld sequencing in some embodiments.

a. Sample Reception—This element may act as a barrier for the sample to escape and can yet be able to accept samples, much like the rubber may top on blood Vacutainers.

b. Lysis Chamber—This illustrates a simple microreactor, chamber which comprises a lysis reagent to break up the cells and to release genomic DNA. This section might also resemble a filter to remove blood cells if the target nucleotide polymer can be free in the blood serum.

c. Nucleic Acid Sample Preparation—The nucleotide polymer fraction of the sample can be isolated and extracted from the rest of the sample constituents (proteins, carbohydrates, lipids, etc). This can be achieved by some methods well known to those skilled in the art. For instance, this maco-fluidic chamber might contain Nexttec's filter technology.

d. Amplification of the Target Nucleotide Polymer—This section may amplify the target nucleotide polymer, using the polymerase chain reaction, which may employ heating elements or other well known strategies of cycling a reaction mix through the different temperatures required for PCR, to perform the thermal cycling required, or isothermal amplification methods (such as LAMB, RPA, etc), which may not require heating of the sample.

e. Sample Processing—This might be required at least in some embodiments to concentrate the nucleic acids, or remove 'over-hang' nucleotide chains that might cause background signal, prior to sequencing.

f. General Microfluidics—This describes the size of the channels, fluid flow, valves and control, materials and valves used in some embodiments.

g. Metal Connects—These connect the sensitive detection nanostructures (in this case, nanowires) to the detector device in some embodiments.

h. Sensitive Detection Nanostructure Arrays—The microfluidics channel can be tightly arrayed sensitive detection nanostructures (such as nanowires, or carbon nanotubes). Two methods of positioning DNA in the channel can be employed; 1. tight channels may allow long stretches of DNA to uncoil, migrate & stretch down the channels which may allow for long read lengths if necessary, and 2. tiling probe/primers can be spotted on to nanowire clusters and short multiple parallel sequencing reactions performed throughout the channels.

i. This weaving microfluidic channel can be filled with reagents in some embodiments, separated by air bubbles. As this microfluidics channel can be pumped, or a tiny actuator moves the reagents along, the sequence of the reagents in the microfluidics channel can run the sequencing by synthesis reaction.

What is claimed is:

1. A method of sequencing a target polynucleotide, comprising:

providing within an assay region a sensitive detection nanostructure that generates a signal related to a charge property within the assay region, wherein the sensitive detection nanostructure is operably coupled to a signal detector;

hybridizing a primer to the target polynucleotide that is operably coupled to the sensitive detection nanostructure, such that the resulting primer-target polynucleotide is operably coupled to the sensitive detection nanostructure;

adding one or more nucleotides and a polymerase to the primer-target polynucleotide within the assay region under conditions that support polymerization of a nascent chain when at least one of the added nucleotides is complementary to the base on the target polynucleotide downstream of the primer, wherein the added nucleotide comprises a charge mass reporter moiety comprising a high charge mass moiety and a linker; and detecting a change in the signal within the assay region upon addition of said nucleotide, wherein the change in the signal is characteristic of the at least one nucleotide added to the nascent chain and wherein the charge mass reporter moiety is removed from the added nucleotide after detecting the signal.

2. The method of claim 1, wherein the charge property is sufficient to result in a detectable change in resistance of the nanostructure.

3. The method of claim 1, wherein the charge mass reporter moiety is configured to be removable.

4. The method of claim 1, wherein the charge mass reporter moiety is configured not to affect polymerization of the nascent chain by the polymerase.

5. The method of claim 1, wherein the charge mass reporter moiety is configured to protrude out from the nascent chain so as to reach-down to the sensitive detection nanostructure.

6. The method of claim 1, wherein the high charge mass moiety comprises an aromatic and/or aliphatic skeleton comprising one or more of a tertiary amino group, an alcohol hydroxyl group, a phenolic hydroxy group, and any combinations thereof.

7. The method of claim 1, wherein the high charge mass moiety comprises one or more of the following groups or derivatives thereof:

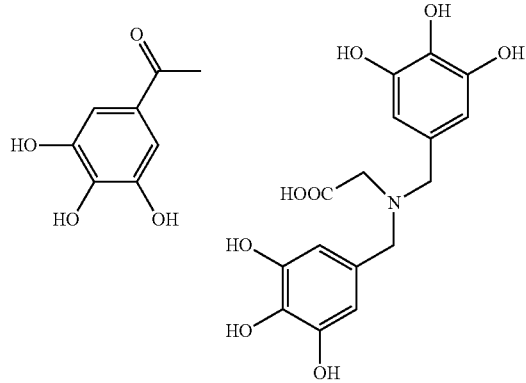

-continued

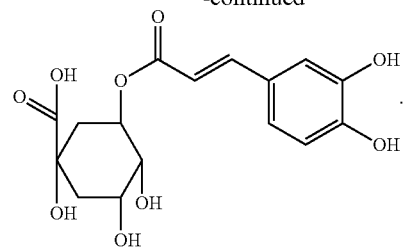

8. The method of claim 1, wherein the linker comprises a molecule of the following general formula:

H$_2$N-L-NH$_2$ wherein L comprises a linear or branched chain comprising an alkyl group, an oxy alkyl group, or a combination thereof.

9. The method of claim 8, wherein L comprises a linear chain comprising an alkyl group, an oxy alkyl group, or a combination thereof.

10. The method of claim 9, wherein a number of carbon atoms in the linear chain is 1 to 100.

11. The method of claim 1, wherein the added nucleotide further comprises a cleavable cap molecule at the 5' phosphate group so that addition of another nucleotide is prevented until the cleavable cap is removed.

12. The method of claim 1, wherein the linker is bound to the 5' phosphate group of the added nucleotide, thereby acting as a cap.

13. The method of claim 1, wherein more than one nucleotides are added to the assay region, but wherein a successive nucleotide is not added to the nascent chain until after the signal that is characteristic of the preceding nucleotide added to the nascent chain is detected.

14. The method of claim 1, wherein the operable coupling between the primer-target polynucleotide and the nanostructure comprises immobilization of the primer to the sensitive detection nanostructure.

15. The method of claim 1, wherein the operable coupling between the primer-target polynucleotide and the nanostructure comprises immobilization of the target polynucleotide to the sensitive detection nanostructure.

16. The method of claim 1, wherein hybridizing the primer to the target polynucleotide comprises hybridizing the primer to an oligonucleotide that has been ligated to the 5' end of the target polynucleotide.

17. The method of claim 1, wherein the sensitive detection nanostructure is selected from the group consisting of a nanowire, a nanotube, a nanogap, a nanobead, a nanopore, a field effect transistor (FET)-type biosensor, a planar field effect transistor, and any conducting nanostructures.

18. The method of claim 1, wherein the target polynucleotide and the primer comprise molecules selected from the group consisting of DNA, RNA, peptide nucleic acid (PNA), morpholino, locked nucleic acid (LNA), glycol nucleic acid (GNA), threose nucleic acid (TNA), synthetic nucleotide polymer, and derivatives thereof.

19. The method of claim 1, wherein the added nucleotide comprises a molecule selected from the group consisting of a deoxyribonucleotide, a ribonucleotide, a peptide nucleotide, a morpholino, a locked nucleotide, a glycol nucleotide, a threose nucleotide, a synthetic nucleotide, and derivatives thereof.

* * * * *

UNITED STATES PATENT AND TRADEMARK OFFICE
CERTIFICATE OF CORRECTION

PATENT NO. : 9,938,573 B2
APPLICATION NO. : 15/228950
DATED : April 10, 2018
INVENTOR(S) : Jonathan O'Halloran It is certified that error appears in the above-identified patent and that said Letters Patent is hereby corrected as shown below:

On the Title Page

Item (63) Related U.S. Application Data, at Line 2, Change "Sep. 3, 2006" to --Sep. 3, 2009--.

In the Specification

In Column 4 at Line 20 (Approx.), Change "1 A" to --1A--.

In Column 9 at Line 20, Change "O-methylphophoroamidite" to --O-methylphosphoramidite--.

In Column 10 at Line 57, Change "Where," to --where,--.

In Column 11 at Line 12 (Approx.), Change "$CH_{2+1}$," to --$C_nH_{2n+1}$,--.

In Column 11 at Line 14 (Approx.), Change "C—$H_2$—OH," to --$C_nH_{2n}OH$,--.

In Column 17 at Line 55 (Approx.), Change "all" to --al.--.

In Column 19 at Line 48, Change "Adenince," to --Adenine,--.

In Column 19 at Line 48, Change "cytoisine" to --cytosine--.

In Column 19 at Line 48, Change "Thyomine" to --Thymine--.

In Column 19 at Line 49, Change "sequenntially)" to --sequentially)--.

In Column 21 at Line 18, Change "too," to --to,--.

In Column 24 at Line 63, Change "posses" to --possess--.

Signed and Sealed this
Fourth Day of September, 2018

Andrei Iancu
*Director of the United States Patent and Trademark Office*

CERTIFICATE OF CORRECTION (continued)
U.S. Pat. No. 9,938,573 B2

In Column 25 at Line 63, Change "ration," to --ratio,--.

In Column 27 at Line 20, Change "on" to --one--.

In Column 27 at Line 34, Change "cantalevers," to --cantilevers,--.

In Column 27 at Line 35, Change "zempto-," to --femto-,--.

In Column 28 at Line 40, After "reactions" insert --.--.

In Column 30 at Line 34, Change "1 A." to --1A.--.

In Column 32 at Line 8 (Approx.), Change "maco-fluidic" to --macro-fluidic--.

SEQUENCE LISTING

```
<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: Exemplary DNA Sequence

<400> SEQUENCE: 1
agtcatcgta gct                                                        13
```